United States Patent [19]
Robinson et al.

[11] Patent Number: 5,895,857
[45] Date of Patent: Apr. 20, 1999

[54] MACHINE FAULT DETECTION USING VIBRATION SIGNAL PEAK DETECTOR

[75] Inventors: James C. Robinson, Knoxville; Brent Vanvoorhis, Kingston; Wojtek Miller, Knoxville, all of Tenn.

[73] Assignee: CSI Technology, Inc., Wilmington, Del.

[21] Appl. No.: 08/840,844

[22] Filed: Apr. 17, 1997

Related U.S. Application Data

[63] Continuation of application No. 08/555,296, Nov. 8, 1995, abandoned.

[51] Int. Cl.$^6$ .................................................. G01N 29/00
[52] U.S. Cl. ........................................ 73/660; 73/602
[58] Field of Search ........................... 73/593, 660, 602, 73/658, 659; 340/683, 679, 680; 702/35, 56, 171

[56] References Cited

U.S. PATENT DOCUMENTS

| | | |
|---|---|---|
| 3,842,663 | 10/1974 | Harting et al. |
| 4,007,630 | 2/1977 | Noda |
| 4,354,378 | 10/1982 | Oshiage et al. |
| 4,366,544 | 12/1982 | Shima .................................. 73/660 |
| 4,422,333 | 12/1983 | Leon |
| 4,429,578 | 2/1984 | Darrel et al. |
| 4,493,042 | 1/1985 | Shima et al. |
| 4,608,650 | 8/1986 | Kapadia |
| 4,790,190 | 12/1988 | Bambara et al. |
| 4,931,949 | 6/1990 | Hernandez et al. |
| 5,109,700 | 5/1992 | Hicho |
| 5,249,138 | 9/1993 | Piety, Jr. et al. |
| 5,646,350 | 7/1997 | Robinson ............................. 73/602 |

*Primary Examiner*—Christine K. Oda
*Attorney, Agent, or Firm*—Luedeka, Neely & Graham, P.C.

[57] ABSTRACT

A signal processing device for processing a machine vibration signal includes a peak value detector for determining the peak vibration amplitude values during predetermined sample time periods. In one embodiment, the vibration signal is digitally processed prior to receipt by a digital peak value detector. In another embodiment, analog processing and peak value detection of the vibration signal is employed. The peak values are then made available for further processing. In many situations, the peak values will be associated with mechanical faults which will be detected at periodic rates corresponding to the mechanical component defect frequencies without additional signal enhancement. Further enhancement can be acquired by synchronous averaging the peak values with the speed of a rotating element. A signal representing the speed of a rotating element (target element) may be obtained directly from a speed sensor that is measuring the speed of the target element, or if the target element is inaccessible, a corrected pseudo-speed signal can be calculated from the speed of an accessible rotating element that is linked to the target element. Transformation of synchronous amplitudes to the frequency domain by means of a fast Fourier transform reveals information that can be used to assess whether or not a fault is present in the rotating machine element.

30 Claims, 20 Drawing Sheets

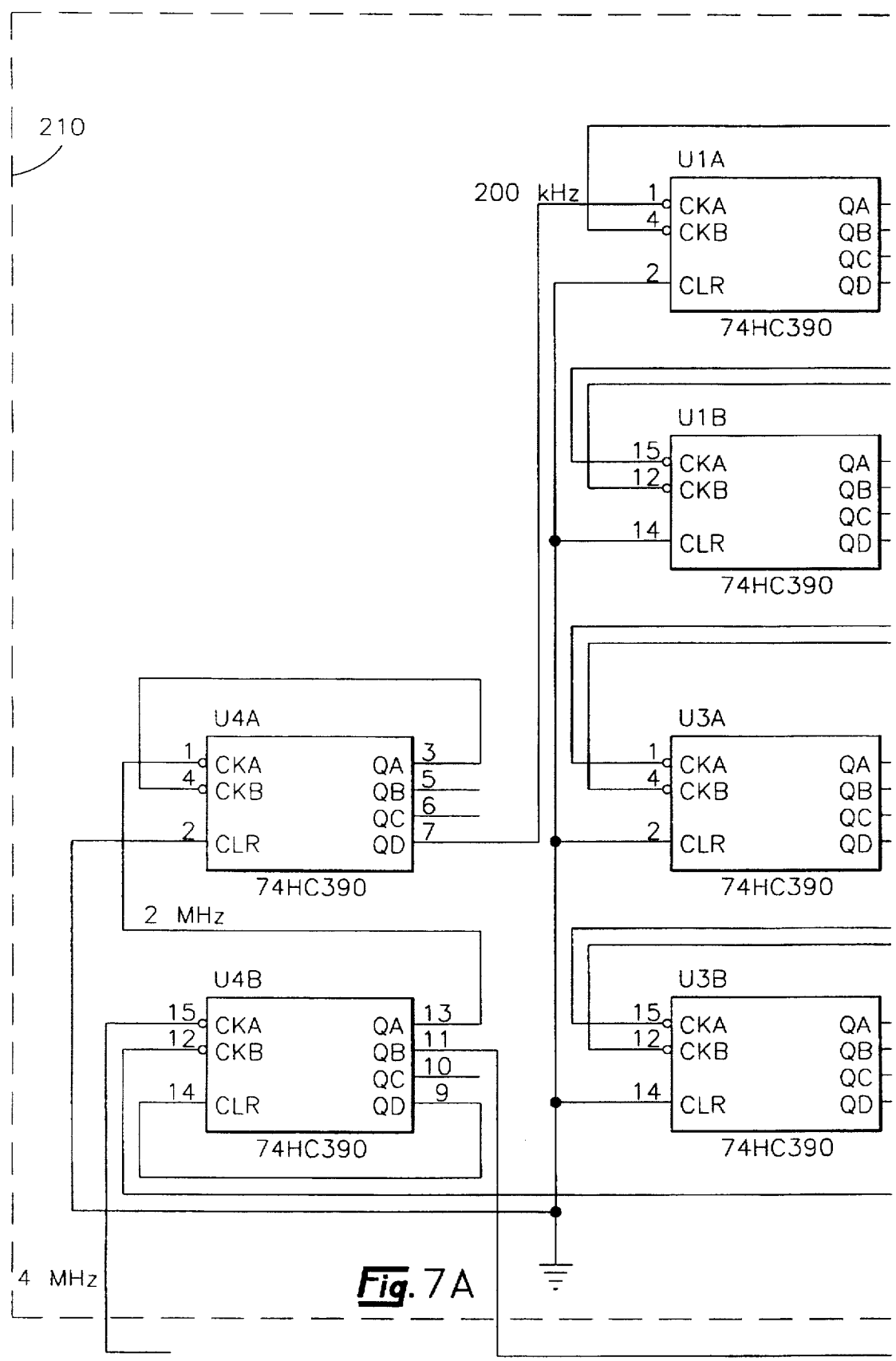

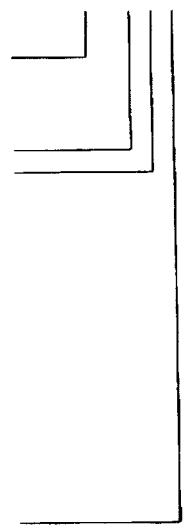
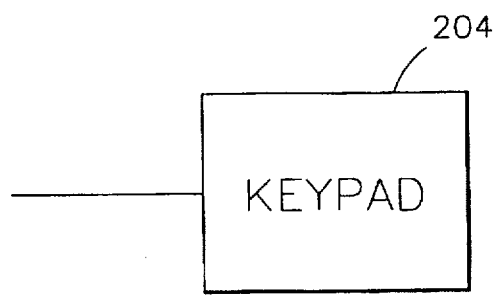
Fig. 7J

MACHINE FAULT DETECTION USING VIBRATION SIGNAL PEAK DETECTOR

This application is a continuation of application Ser. No. 08/555,296, filed Nov. 8, 1995, which is abandoned.

TECHNICAL FIELD

The present invention relates to a method and apparatus for nonintrusive detection of faults in machines having rotating or reciprocating elements. More particularly, the present invention relates to a diagnostic system and method of detecting faults in rotating or reciprocating machine elements such as gears and bearings.

BACKGROUND OF THE INVENTION

Today, most manufacturing processes require complex industrial machines utilizing rotating or reciprocating elements. The efficient operation and maintenance of these machines is essential to maximizing production and minimizing downtime. When a rotating machine element acquires a defect, that defect is seldom catastrophic at onset. Instead, the defect is usually of a latent or incipient nature, such as a hairline fracture in the tooth of a gear. Notwithstanding a probable reduction in the efficiency of the machine, if such a fault is not detected, isolated, and repaired it could grow into a catastrophic failure of the machine with resultant loss of production and possible injury to personnel. Unfortunately, due to the noise generated by these machines and the acoustic environment in which they normally operate, it is often difficult if not impossible to detect latent or even incipient defects in rotating elements of the machine by visual or aural inspection. Further complicating the detection of such faults is that faulty components may be hidden from view, such as a single gear in an enclosed gearbox.

It is desirable to detect and locate faults while the machine is operating in its normal environment so as not to interfere with the production process. Taking the machine off line to perform predictive maintenance creates an undesirable and inefficient situation, requiring a back-up or redundant machine in order to prevent a shutdown of the production process.

It is known that a defective rotating or reciprocating machine element will generate periodic vibrations as the defect comes into contact with other machine elements along its path of rotation. For example, a roller bearing having a hairline fracture will generate a vibration each time the fracture contacts another machine element, generating a periodic series of vibrations. In U.S. Pat. No. 5,109,700 to Hicho, these periodic vibrations are detected by a vibration transducer attached to the machine. The transducer converts the vibrations into an electrical signal which is filtered to obtain selected frequencies of the electrical signal. The filtered electrical signal is then converted into a frequency spectrum by a fast Fourier transform. Random or spurious components are eliminated leaving only frequency components that are representative of the machine running speed. Corresponding frequency components remaining are averaged, and the highest average amplitude value is used as a bearing condition indicator.

Another prior art approach to detecting faults in rotating machine elements is that disclosed in U.S. Pat. No. 4,007,630 to Noda. Noda describes a device for detecting damage to rotators, such as ball bearings. Mechanical oscillation is converted into an electric signal, and the peak values of this electric signal are detected, retained for a period of time, and reset to zero. The output signal is fed into a smoothing integrator to extract a mean value from which the presence of a rotator fault is determined.

In U.S. Pat. No. 4,931,949 to Hernandez et al., a gear defect analyzing system is disclosed. Signals from an accelerometer and a shaft encoder pass through full wave rectifiers and low pass filters in order to extract the amplitude envelope, which is then converted to a digital signal for analysis by a microcomputer. A Top-Dead-Center pulse (once per shaft revolution pulse) is added to ensure that an encoder pulse was not missed. Time history analysis is performed on the signal, and tooth-to-tooth interaction is recorded until the pattern begins to repeat. Subsequent recordings are averaged with respect to previous records to produce a unique pattern to identify which tooth-to-tooth interaction is likely to involve defective teeth.

A consideration which the prior art fails to account for involves the trade-off that exists between the required sampling rate of a vibration signal and the time record length. Generally, an impact or other event of interest will generate a signal which lasts for only a few milliseconds at best. As a result, the envelope of this signal will only be present for a few milliseconds, typically 5 to 10. A minimum sampling rate in the ten to fifty thousand samples per second range must be employed to capture an event of such short duration, and a typical time record could demand a system capable of storing up to 3,000,000 samples. With a large computer, records of this size can be dealt with, but large computers are generally not very portable and are difficult to use in a typical industrial setting where many machines are periodically monitored for faults. In addition, typical field portable data collectors/analyzers are incapable of handling extremely large time records. Therefore, there is a need for a highly portable fault detection system that is capable of employing existing field portable data collectors while ensuring that events of interest are captured within the time record.

Variations in gear ratios due to "slop" in the gear train are another impediment to accurate vibration analysis. If one is attempting to analyze a rotating element that is buried within a gearbox, it is known to use a shaft speed indicator signal, or tachometer signal, from another shaft in the gear train that is easily accessible and then multiply or divide that tachometer signal by the gear ratio to arrive at a corrected speed representative of the rotating element under analysis. However, there is often considerable slack or slop in most gear trains, and this slop will cause errors in the tachometer signal which will introduce errors when the tachometer signal is synchronously averaged with a vibration signal. This error is particularly amplified where the shaft being monitored by the tachometer is a relatively slowly rotating shaft, and the gear of interest is rotating at a relatively high frequency. In such a case, it is likely that the averaging will totally eliminate the frequencies of interest because the tachometer signal will not be properly synchronized with the high speed gear. Adding to this problem is the natural high frequency signals that are produced by impacting gear teeth. These high frequency impact signals are the most telling of a cracked tooth, but their high frequency makes them most susceptible to being averaged out during synchronous averaging should the tachometer signal be slightly asynchronous.

SUMMARY OF THE INVENTION

Regarding the foregoing and other objects of the invention, the present invention provides a signal processing device for processing a machine vibration signal generated by a vibration sensor. The device produces a processed vibration signal that is output for further analysis. A peak value detector receives the machine vibration signal and samples it during predetermined sample time periods. The peak amplitude values of the vibration signal are held during each of the sample time periods to produce peak vibration amplitudes which are then output for further processing.

In a preferred embodiment, the device includes an auto ranging amplifier for amplifying the vibration signal according to its strength, producing an amplified vibration signal. A sampling circuit receives the amplified vibration signal and samples it at a predetermined rate. This sampling process effectively digitizes the signal so that a digitized vibration signal is produced. A rectifier receives the digitized vibration signal and full wave rectifies it to produce a rectified vibration signal which is provided to the peak value detector.

In another preferred embodiment, the peak value detector oil the device includes dual peak hold means. A first peak hold means holds the peak amplitude values of the vibration signal during a first sample time period as defined by T−ΔT. A second peak hold means holds the peak amplitude values of the vibration signal during a second sample time period as defined by T+ΔT. The output during the time period T+ΔT is the held peak value experienced by the first peak hold means during the time period T−ΔT. At the end of the time period T+ΔT, the output is switched to the second peak hold means for a time period of duration ΔT. This alternating of the input and output between the two sample hold means is accomplished by analog switching means. Reset means are used to reset the first peak hold means at time T−ΔT, and to reset the second peak hold means at time T.

In accordance with one aspect of this embodiment, a fault detection apparatus receives machine vibration and speed signals. In this embodiment, the apparatus processes the vibration signal to produce a processed vibration signal, and synchronously averages the processed vibration signal at the speed indicated by the speed signal to determine the presence of a fault in an element of a machine that is rotating at the speed indicated by the speed signal. A peak value detector receives the machine vibration signal and samples it during predetermined sample time periods. The peak amplitude values of the vibration signal are held during the sample time periods so that a time series of peak held amplitude values is produced. Clock means are used to generate at least one clock signal for setting the length of the sample time periods. Finally, the apparatus includes means for synchronously averaging the time series of peak held amplitude values (the peak signal) at the speed of the rotating element to produce a time series of synchronously averaged amplitude values.

As mentioned above, slop in a gear train may cause slight frequency changes in the occurrence of an event of interest. For example, vibration caused by a cracked tooth in a gear train may be referred to as "clicks" separated by relatively long time intervals. If slop is present in the gear train, the time intervals may vary and the clicks may be averaged out over time. However, by peak detecting over a sample time period, and by choosing an appropriate sample time period, the "clicks" will produce a peak during the same sample time period even if there are variations in the time intervals between clicks. In other words, the time intervals between clicks may change without changing the sample time period during which the click occurs, and, if so, the peak detector produces the same peak signal despite the changing time intervals between clicks. Thus, when the peak signal is synchronously averaged, the peaks corresponding to the clicks are not averaged out.

The vibration signal may be pre-processed prior to receipt by the peak value detector. This is accomplished with an auto ranging amplifier that amplifies the vibration signal as needed, to produce an amplified vibration signal. For a particularly strong signal, the auto ranging amplifier may attenuate (negatively amplify) the signal. A sampling circuit receives the amplified vibration signal and samples it at a predetermined rate to produce a digitized vibration signal. A rectifier receives the digitized vibration signal and full wave rectifies it, producing a rectified vibration signal that is provided to the peak value detector.

A pseudo-speed circuit is used to reduce errors and to compensate for a rotation ratio between an accessible rotating machine element and a target rotating machine element. This circuit produces a pseudo-speed signal corresponding to the speed of the target rotating machine element. Within the circuit is at filter for eliminating noise from the speed signal to produce a filtered speed signal. A microcomputer receives the filtered speed signal and adjusts the filtered speed signal to reduce errors and compensate for the rotation ratio, producing a pseudo-speed signal. An output buffer holds the pseudo-speed signal so that it can be provided to the means for synchronously averaging. For determining the presence of a fault in the target element, fast Fourier transform means are used to transform the time series of synchronously averaged amplitude values to the frequency domain.

In another preferred embodiment of the present invention, there is disclosed a fault detection system for detecting mechanical faults of machines that have one or more rotating elements, including an accessible element and a target element (which may be the same element if the target element is also accessible). The system includes a vibration sensor for sensing vibrations generated by at least a target rotating machine element during machine operation to produce a vibration signal that contains a plurality of amplitudes and frequencies. A peak value detector samples the vibration signal during predetermined sample time periods and holds the peak amplitude value of the vibration signal during sample time periods, producing a time series of peak held amplitude values. Clock means are used to generate at least one clock signal for setting the length of the sample time periods. A speed sensor senses the speed of an accessible rotating machine element and produces a speed signal. A pseudo-speed circuit receives and adjusts the speed signal to reduce errors and to compensate for a rotation ratio between the accessible rotating machine element and the target rotating machine element, producing a pseudo-speed signal. Finally, there are means for reading the time series of peak held amplitude values, receiving the pseudo-speed signal, and synchronously averaging the time series of peak held amplitude values at the speed indicated by the pseudo-speed signal, producing a time series of synchronously averaged amplitude values for determining the presence of a fault in the target rotating machine element.

In a preferred embodiment of the present invention, there is disclosed a method of processing, for further analysis, a machine vibration signal generated by a vibration sensor. The method includes the steps of sampling the vibration signal during predetermined sample time periods, and detecting the peak amplitude value of the vibration signal with a peak value detector during the sample time periods. The peak vibration amplitudes are then output for further processing or analysis.

In another preferred embodiment, a method of detecting faults in a machine having rotating machine elements, which elements include at least an accessible element and a target element, includes the steps of producing a vibration signal containing amplitudes and frequencies. The vibration signal is sampled during predetermined sample periods of time. The peak amplitude value of the vibration signal is held during each sample period of time, producing peak held amplitude values which are read at a predetermined rate to produce a time series of peak held amplitude values. A speed signal, representative of the speed of the target element, is produced with a speed sensor. The time series of peak held amplitude values are synchronously averaged at the speed indicated by the speed signal, producing a time series of synchronously averaged amplitude values, which are then transformed to the frequency domain to determine the presence of a fault in the target element.

BRIEF DESCRIPTION OF THE DRAWINGS

The invention will now be described in further detail with reference to the drawings wherein like reference characters designate like or similar elements throughout the several drawings where.

DETAILED DESCRIPTION OF THE PREFERRED EMBODIMENT

Figure 1:
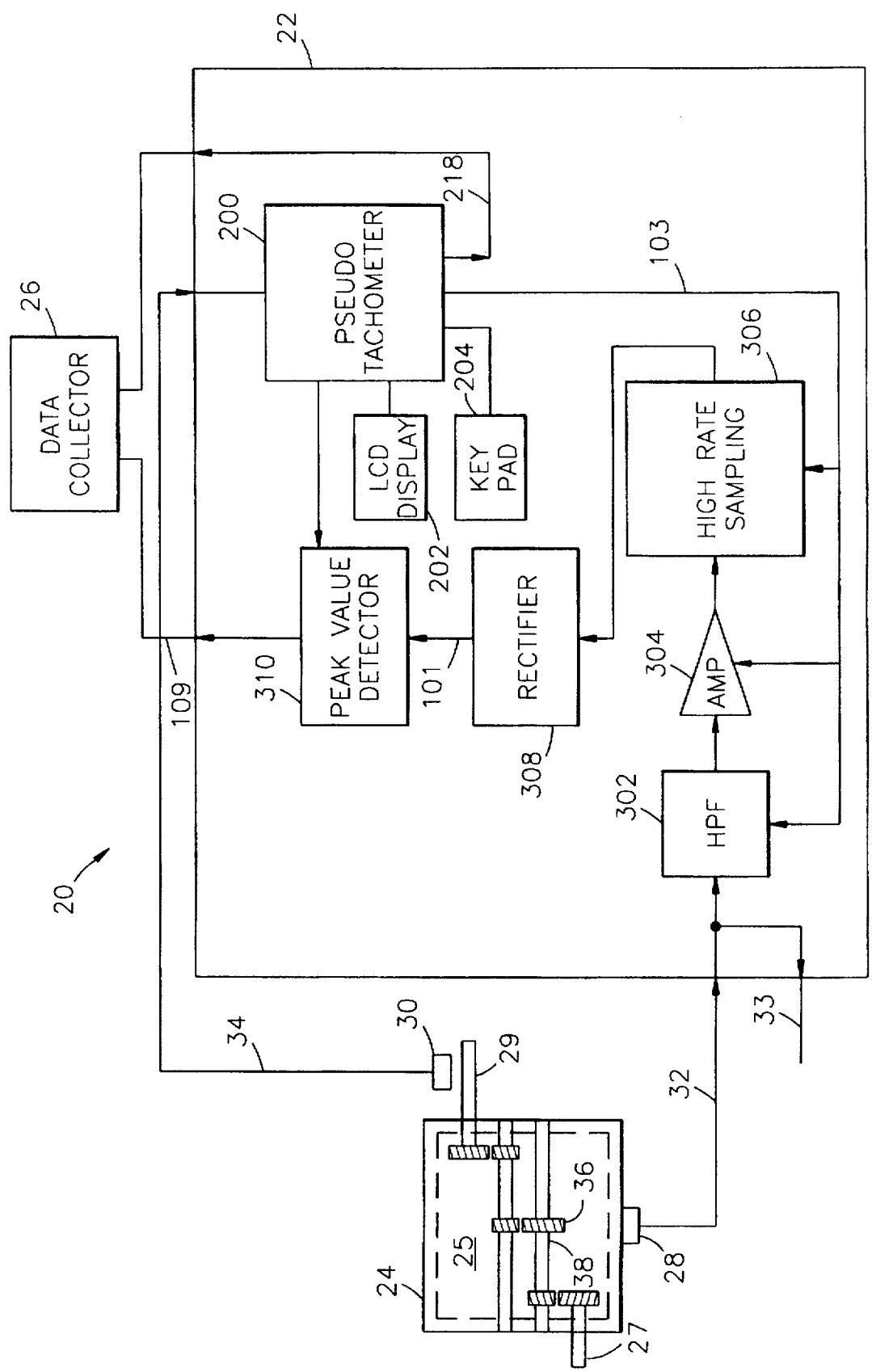
FIG. 1 is a block diagram illustrating a predominantly digital embodiment of the fault detection system of the present invention.

As shown in FIG. 1, a fault detection system 20 for detecting faults of rotating elements within, for example, a gearbox 24 having an input shaft 27, an output shaft 29, and a gear train 25 includes a signal processing unit 22 which receives an input from vibration sensor 28 on line 32 and a shaft speed sensor 30 input on line 34. To determine whether a particular rotating element within the gearbox 24 has a fault, such as target gear 36, vibration signals (including normal vibrations and stress wave, or impact, vibrations) generated by the gearbox 24 are processed to determine the peak values of the signal. Thee peak values are then analyzed to determine whether or not a fault exists with respect to the target gear 36.

In one preferred embodiment, the peak values are synchronously averaged at the speed of the gear 36 by data collector/analyzer 26. Normally, the high frequency vibration signal from a fault event (stress wave) such as a fractured gear tooth would be difficult to detect because the gearbox 24 produces many different normal vibration components. However, by synchronously averaging at the speed of the gear, the normal vibration components will average out and only synchronous vibration signals will remain.

Vibrations generated by target gear 36, as well as other rotating elements of the gearbox 24, are sensed by vibration sensor 28, which is typically an accelerometer 28. The analog output of accelerometer 28 is received by the signal processing unit 22 where it is appropriately processed and provided to a data collector 26, such as a CSI 2115 or 2120, preferably for synchronous averaging at the speed of target gear 36. Alternatively, the processed vibration signal may be visually analyzed to assess whether or not a fault is likely to be present.

As shown in the preferred digital embodiment of FIG. 1, the accelerometer output on line 32 is received by a high pass filter 302 to produce a filtered signal. While this embodiment employs a high pass filter to help eliminate noise from the accelerometer signal, it will be understood that the high pass filter 302 is not a required element of the design. The filtered signal is auto ranged by amplifier 304 to increase or decrease signal strength as necessary. If the signal is weak it will be amplified. If the signal is particularly strong, the auto ranging amplifier 304 will attenuate, or negatively amplify the signal. The auto ranged signal is received by a high rate sampling circuit 306 and sampled at a high rate so that the signal is effectively digitized. In a preferred embodiment, the signal is sampled at a rate of 100K samples per second. The digitized signal is full wave rectified by digital rectifier 308 to produce a rectified signal. Finally, digital peak value detector 310 identifies and saves the maximum value of the signal occurring over a predetermined time interval. In a preferred embodiment, at least the digital rectifier 308 and the peak value detector circuit 310 are implemented in a microprocessor based computer or data collector 26, such as a CSI 2115 or 2120 data collector.

To ensure accuracy during synchronous averaging, the collected vibration data should be synchronized as nearly as possible with the angular position of the target gear 36. This is done by synchronizing the collected data with the rotational speed of the gear 36. Because the target gear 36 is often buried within the gearbox where there is no access to the gear's shaft 38, its speed cannot be measured directly, but instead, must be calculated from the known speed of some other rotating element within the gear train 25. A speed sensor, such as a tachometer 30, is used to obtain a tachometer signal (speed signal) from an accessible shaft in the gear train 25, such as an output shaft 29, which is then multiplied or divided by the appropriate gear ratio between the target gear 36 and the output shaft 29 to arrive at a calculated speed for the target gear 36; i.e., the tachometer signal is multiplied by the ratio of the accessible output shaft 29 to the target gear 36 to determine the speed of the target gear 36.

It will be understood that the speed of any accessible shaft or other rotating element forming a part of the gear train 25, including input shaft 27 and output shaft 29, may be used to calculate the speed of the target gear 36, so long as the gear ratio between the accessible shaft and the target gear 36 is known. It will be further understood that the accessible rotating element may also function as the target rotating element to enable the detection of mechanical faults within the accessible element. In this case, the rotation ratio is unity and a speed signal representing the speed of the target gear 36 may be obtained directly from the speed sensor, or tachometer 30, without the need for further processing of the speed signal.

The output of tachometer 30 is received by the signal processing unit 22 where it is adjusted to reduce errors and to compensate for a rotation ratio, or gear ratio between the output shaft 29 and target gear 36, producing a pseudo-speed, or pseudo-tachometer signal that is provided to the data collector 26 for use during synchronous averaging, as will be more fully described herein. Alternatively, the signal processing unit 22 may perform the synchronous averaging, or the data collector 26 may perform the functions of the signal processing unit 22. In the embodiment of FIG. 1, the data collector 26 synchronously averages the vibration signals at the speed of the target gear 36 using the pseudo-tachometer signals to determine whether the target gear 36 is faulty. In applications where the speed of the target gear, or monitored element, can be directly measured (i.e., the element is accessible), producing a pseudo-tachometer signal is unnecessary. Instead, the tachometer signal on line 34 may be utilized directly from the tachometer output.

Peak values of the vibration signal, detected by peak value detector 310 and output on lines 109, must now be provided to the data collector 26 for synchronous averaging with the pseudo-tachometer signal. To provide a system that is highly portable, a normal data collector such as the CSI 2115 or 2120 is preferred. Data collectors are typically designed to deal with data block sizes that fit FFT requirements (sizes of $2^n$). The most popular block size is 1024, although other sizes can be used. Dealing with such a small data block size tends to amplify the trade-off between the signal sampling rate and the data record size, particularly when monitoring for bearing defects where the event duration is typically shorter than for gear defects. The problem is that an event of interest (impact) generates a signal (typical carrier frequency of a few kilohertz) which has a time duration of a few milliseconds, so that the envelope of the impact will only be present for a few milliseconds (usually 5 to 50). To capture this short lived event, a minimum sample rate in the mid thousands of samples per second range must be maintained by the data collector 26 over a period of time. If the rotating element being monitored is a bearing on a slow turning shaft, a time record length in the range of several seconds to minutes must be established.

As an example of the foregoing discussion, suppose it is desired to monitor a bearing on a shaft turning at 10 rpm for at least 20 revolutions of the shaft. This would require a time record length of 120 seconds. It should be noted that the interest here is in an impact indicating the presence of a fault. To be sure that impact events are captured, a sample rate of approximately 2000 samples or more per second would need to be maintained. This would create a data record size of about 240,000 data points. Microcomputers can handle records of this size, but the trade-off here is between memory capacity and system portability. Because of their size and bulk, microcomputers are simply not well suited for field operations, particularly in applications where a large number of machines spaced at different locations are to be monitored. On the other hand, normal data collectors are well suited for use in the field, but typically are not well suited for handling large data blocks.

For an $f_{max}$ of 10 Hz, a portable data collector maintains a minimum sampling frequency of 25.6 samples/sec to avoid aliasing. For a selected $f_{max}$ of 10 Hz (sampling frequency of 25.6), and a selected block size of 400 frequency lines, the sampled block of 1024 data points would take 40 seconds to fill. Selecting 1,600 frequency lines would take 160 seconds to fill. Sampling at a rate of 25.6 samples per second results in a sample being captured every 39 msec. If one were sampling a raw signal, the peaks of the impact event would be entirely missed many times and, resultingly, would be averaged out.

It has been determined that data collectors such as the CSI 2115 or 2120 can be used to reliably detect short duration impact events, like bearing faults, by employing the peak value detection (PeakVue) methodology of the present invention. Using signal rectification and a peak value (PeakVue) detection methodology, a hold time of greater than 39 msec would guarantee that the impact event would always be detected as represented by its peak amplitude values. This ability to correlate the peak value sampled signal with the sampling rate of the data collector 26 enables one to employ standard or synchronous averaging with standard data collectors to detect mechanical faults on a wide spectrum of machinery, from very slow machines to very fast machines.

Figure 2:
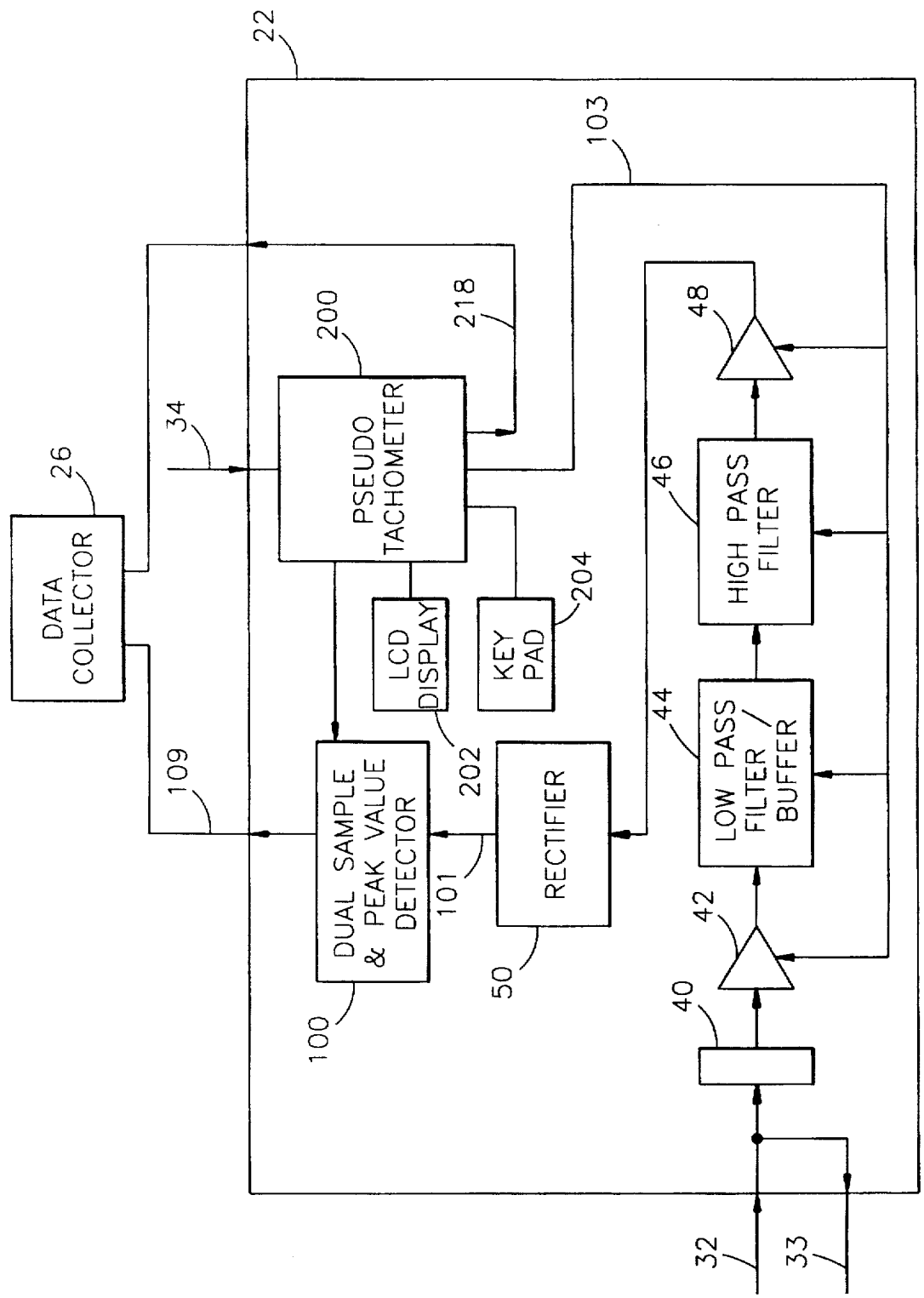
FIG. 2 is a block diagram illustrating a predominantly analog embodiment of the fault detection system of the present invention.

FIG. 2 shows a preferred analog embodiment of the Peakvue methodology for producing peak vibration signal values on lines 109. This embodiment, as well as the digital embodiment of the PeakVue Methodology previously described, may actually be implemented into the data collector 26 so that the vibration signal generated by the accelerometer 28 on line 32 may be directly input to the data collector 26. Vibration signals produced by sensor 28 that are of sufficient quality may be routed directly to a dual sample and peak value detector circuit 100 without any preprocessing of the raw vibration signals. However, to account for inherent weaknesses in the raw accelerometer signal, a preferred embodiment of the invention amplifies, filters, and rectifies the raw signals prior to their peak values being held for reading by the data collector 26. Low frequency components (e.g., usually ranging from 20 to 500 Hz) of the analog accelerometer signal will typically contain information that is unrelated to impacting events. These unwanted components are preferably eliminated by a high pass filter/buffer 40. The filtered accelerometer signal is then amplified by pre-gain amplifier 42 having a user selectable gain. In a preferred embodiment, the amplified accelerometer signal is then bandpass conditioned by means of a low pass butterworth filter 44 and a high pass butterworth filter 46, with the passband frequencies of each filter being user selectable. After being amplified a second time by a post-gain amplifier 48 having a user selectable gain, the vibration signal is in condition for rectification. Preferably, amplification of the accelerometer signal is automatically adjusted according to the strength of the accelerometer signal (auto ranging) so that no amplification would be needed should the accelerometer signal be of sufficient strength when received by the unit 22.

User selectable settings of the pre-gain amplifier 42, post-gain amplifier 48, and passband filters 44 and 46 are entered by means of a keypad 204 located on an external surface of the signal processing unit 22. Appropriate user prompts and corresponding entries are displayed on an LCD display 202. In a preferred embodiment, gain selections for the pre-gain amplifier 42 are 0.1, 1.0,and 10.0, while gain selections for the post-gain amplifier 48 include 1, 10, and 100. Passband frequencies for the filters 44 and 46 include band widths of 50–5,000 Hz, 500–10,000 Hz, 1,500–15,000 Hz, and 5,000–40,000 Hz. Appropriate selections of these parameters will generally depend upon the conditioning that is required of the input signal prior to rectification and sampling. This in turn depends upon the nature and characteristics of the rotating elements being monitored; e.g., gears, bearings, etc.

For example, to monitor the target gear 36 of FIG. 1 for faults, one would typically select a pre-gain of 1 and a post-gain of 10 for a particularly weak vibration signal. Because impacts representative of faults in gears are typically characterized by vibrations of about 10 KHz, a bandpass of 1,500–15,000 Hz would be selected. For a particularly strong vibration signal, the signal may need to be attenuated (negatively amplified) before processing. In such a case, a pre-gain of 0.1 may be selected.

Figure 3:
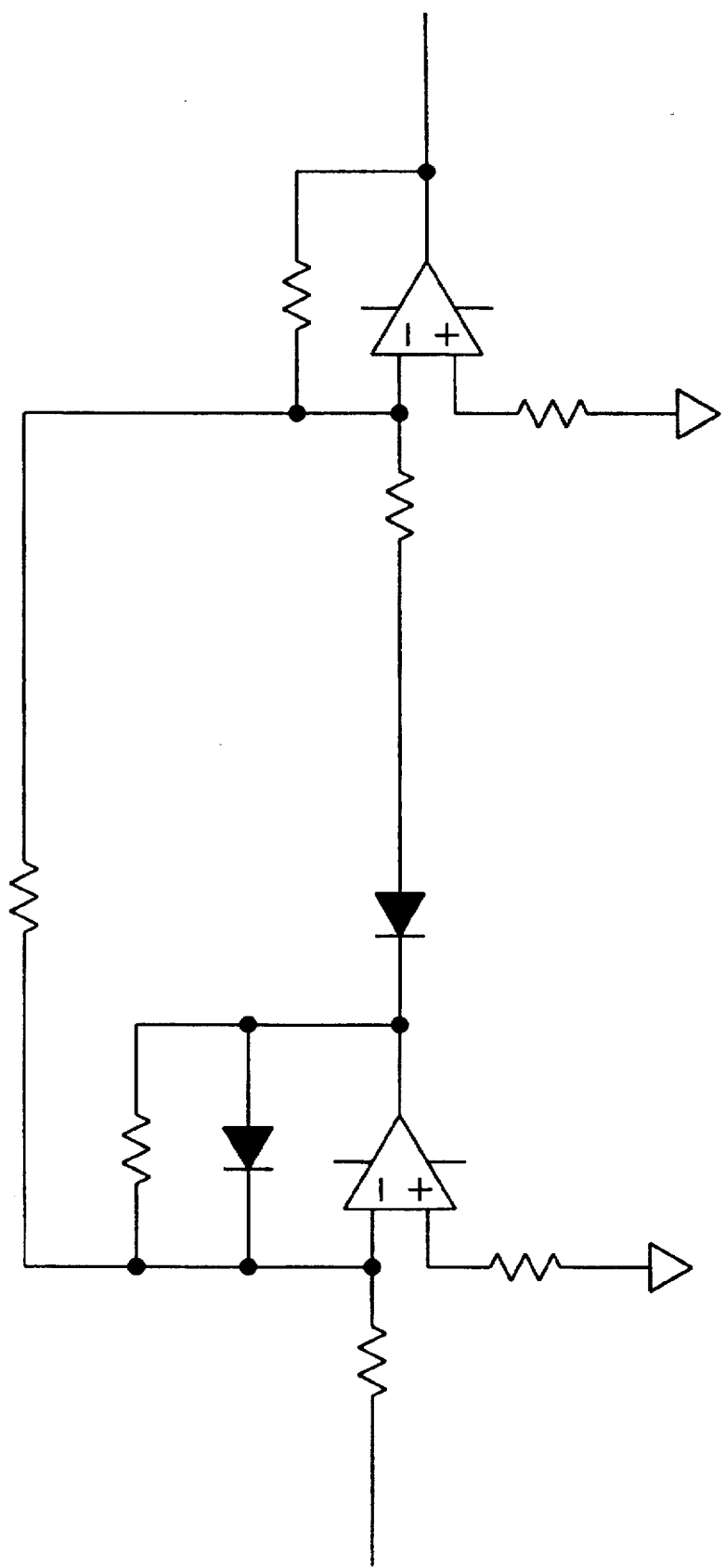
FIG. 3 is a schematic circuit diagram of a rectifier.

The filtered and amplified vibration signal is rectified by full wave rectifier 50 and a rectified signal is created which includes the high frequency impact signal from a meaningful event (impact), such as the meshing of a faulted gear tooth with another gear tooth. A schematic circuit diagram of the full wave rectifier 50 is illustrated in FIG. 3. It should be noted that the vibration signal may be provided to the dual sample and peak value detector circuit 100 without full wave rectification. In such a case, only the positive peaks of the vibration signal would be considered since a positive peak, however small, will always be greater than a negative peak. The full wave rectifier 50 ensures that all amplitude peaks of the vibration signal (including negative peaks) are available for detection by the dual sample and peak value detector circuit 100. Although the consideration of only positive vibration signal peaks is sufficient for purposes of fault detection, it is preferred that the negative peak amplitudes be considered as well.

An advantage of the peak detection methodology described above is that it helps to compensate for minor deviations between the speed as; indicated by the tachometer signal and the true speed of the target gear 36. It has been determined experimentally that a peak detected signal can be synchronously averaged and used to detect broken gear teeth in circumstances where synchronously averaging the vibration signal would not show the broken gear tooth. In other words, the stress wave components of the vibration signal produced by the broken gear tooth will survive synchronous averaging and will be accentuated by such synchronous averaging even if the tach signal is slightly asynchronous, such as the case where slack or slop is present in a gear train. In comparison, without the peak detection described above, the stress wave components produced by the broken gear tooth will be significantly averaged out by the synchronous averaging technique and in many circumstances will be undetectable.

With continued reference to FIG. 2, the rectified vibration signal from full wave rectifier 50 is provided to a dual sample and peak value detector circuit 100 on lines 101 where peak amplitude values of the rectified vibration signal are held for a user specified period of time after which the peak held amplitude values are sampled by the data collector 26 at a user selected rate. While a dual sample and peak value detector circuit is preferred in this embodiment, it will be understood that a peak value detector circuit which employs only one sample and hold device will work.

Figure 4:
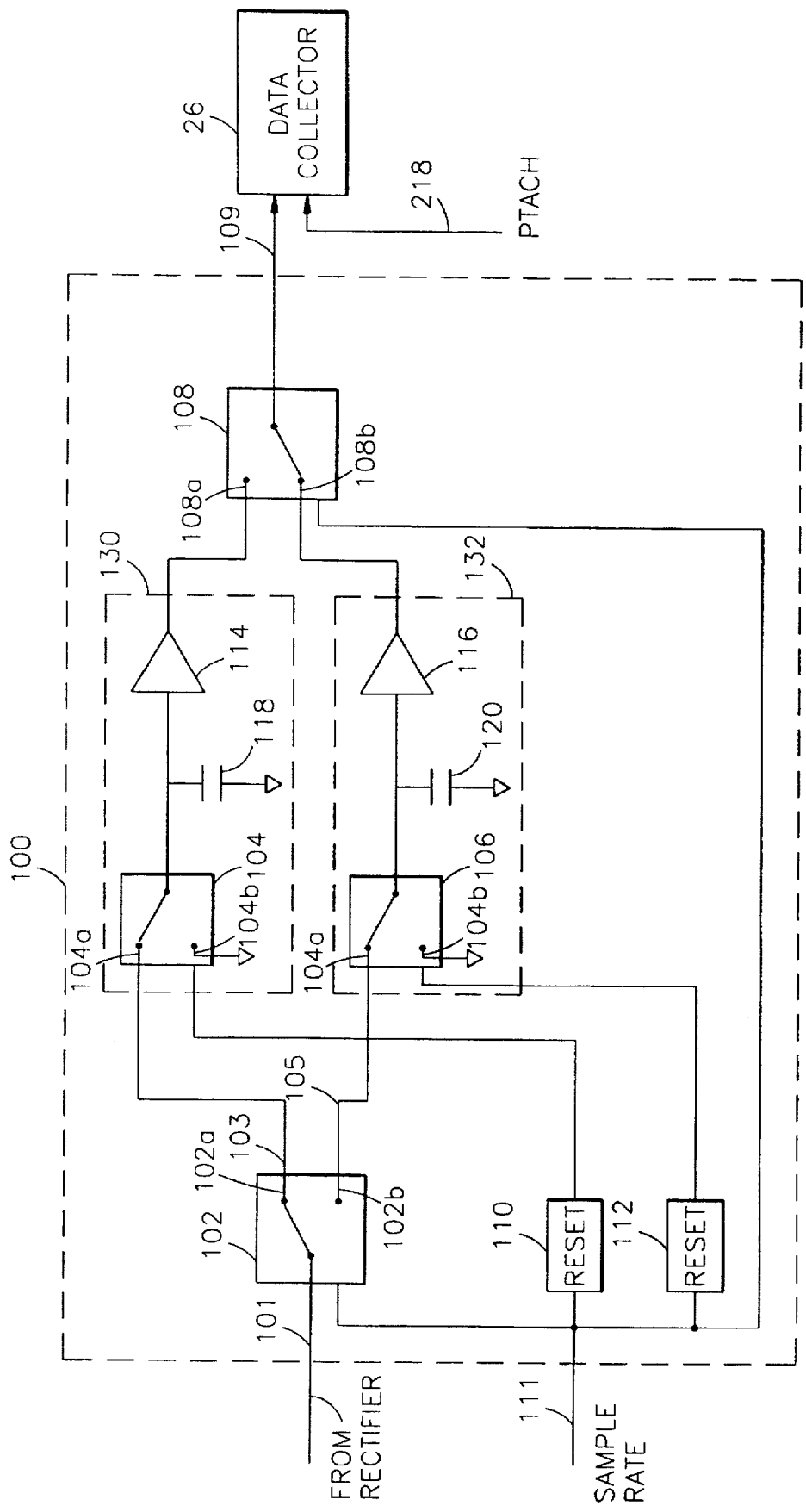
FIG. 4 is a block diagram of dual sample and peak value detector circuitry.
Figure 5A:
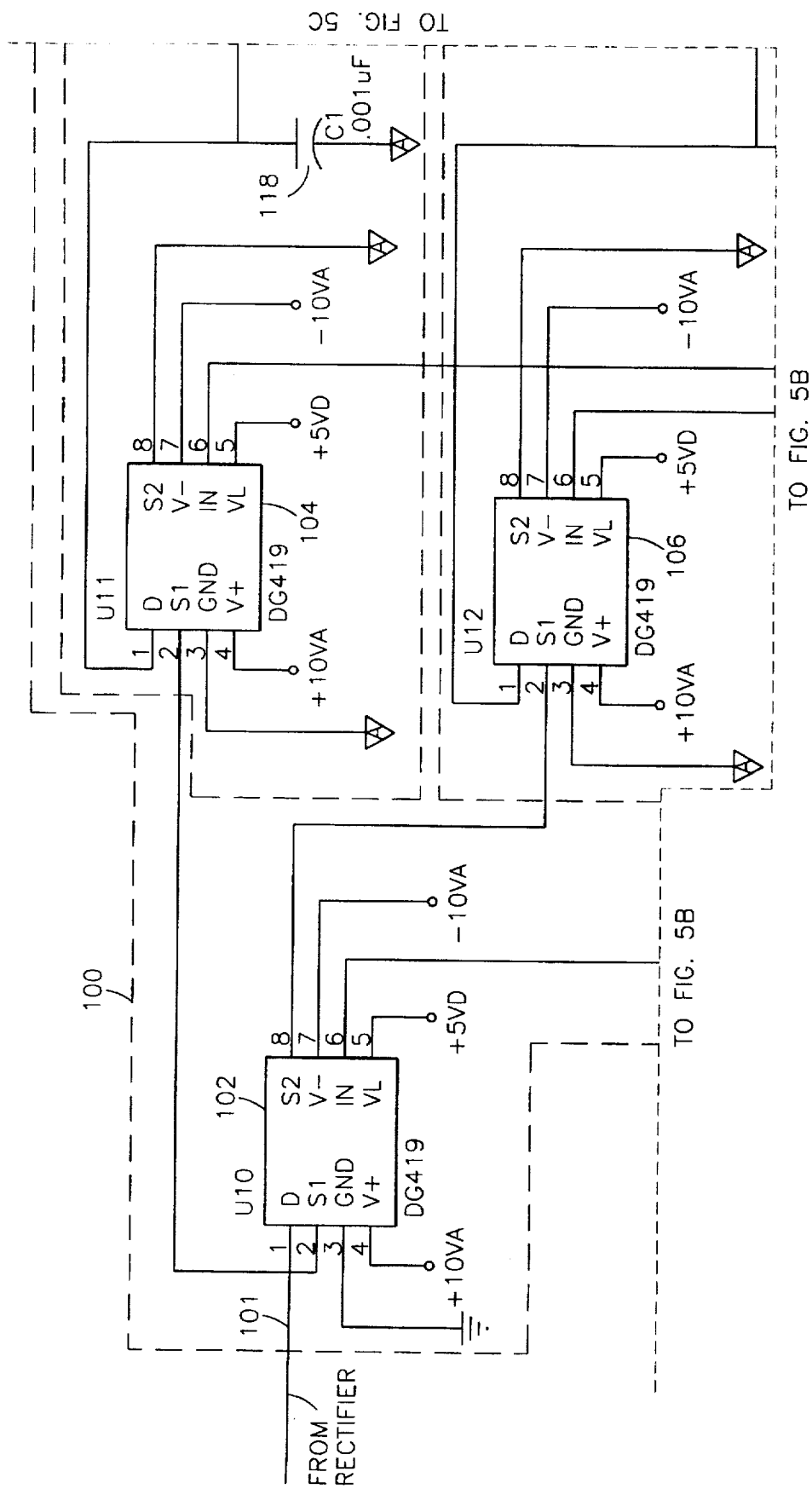
FIGS. 5A, 5B and 5C collectively are a schematic circuit diagram of dual sample and peak value detector circuitry.
Figure 5B:
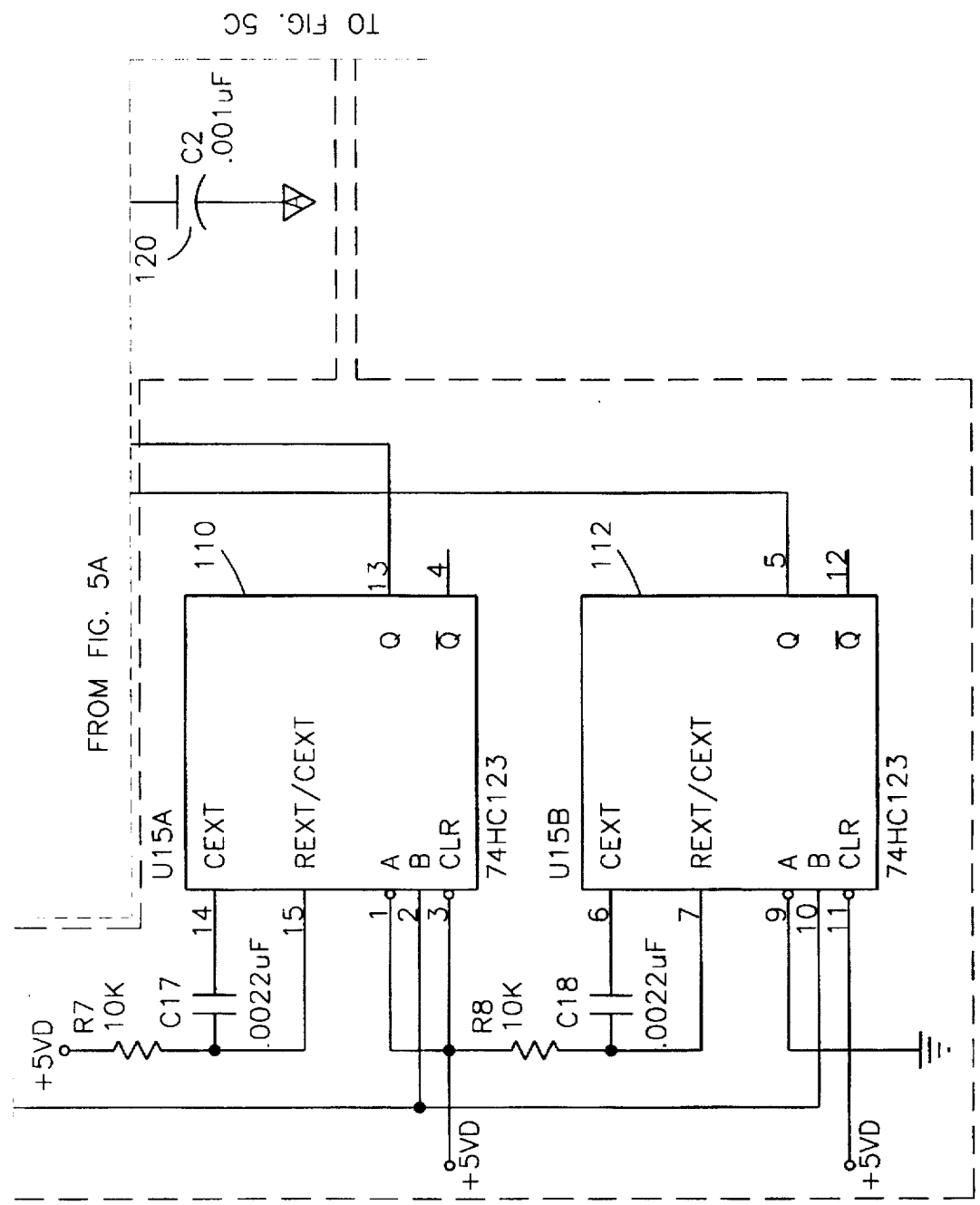
Figure 5C:
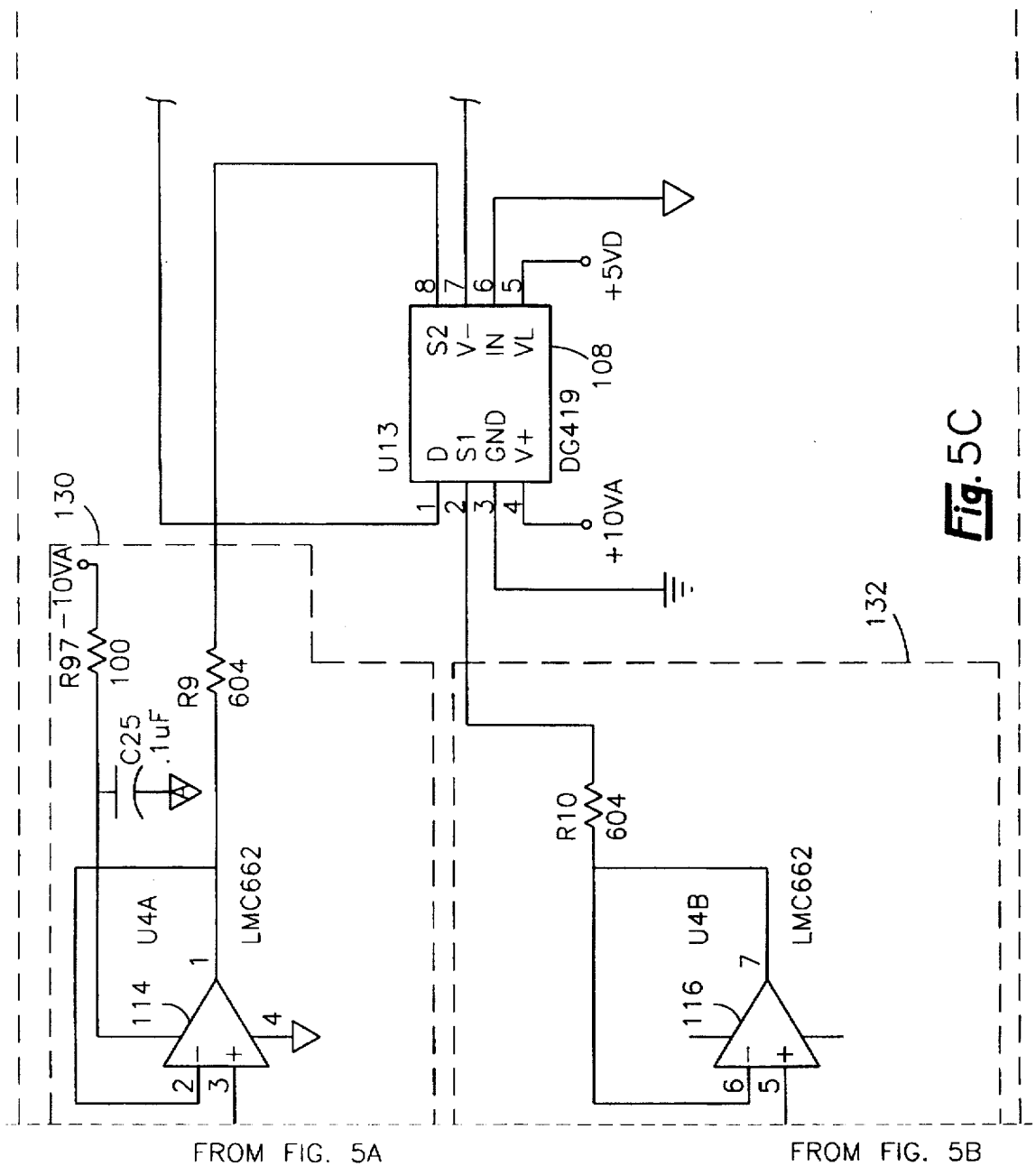

FIG. 4 shows a block diagram of the dual sample and peak value detector circuit 100, while FIGS. 5A, 5B and 5C provide a detailed schematic circuit diagram of the circuit 100. An analog switch 102 having two closed positions receives the rectified vibration signal on lines 101 and alternately routes the rectified vibration signal to peak hold A 130 and peak hold B 132. When the analog switch 102 is in a first closed position 102a, continuity is established with lines 103 so that the rectified vibration signal is routed to peak hold A 130 for a first sample period of time beginning at time T and ending at time T+ΔT. Analog switch 104, having two closed positions, receives the rectified vibration signal on line 103. When analog switch 104 is in a first closed position 104A, the rectified vibration signal is provided to hold capacitor 118 and hold buffer 114. Capacitor 118 is charged to a value representative of the peak amplitude value being routed through analog switch 104. Hold buffer 114 continually holds the most current peak value represented by the charge on capacitor 118. When switch 102 is in a second closed position 102B, analog switch 108, having two closed positions, is simultaneously switched to a first closed position of 108A. Continuity is established with line 109 and the peak held value is provided to the data collector 26. Data collector 26 reads the peak held value of hold buffer 114 at the user specified sample rate.

Switch 102, remaining in a second closed position 102B, establishes continuity with lines 105, thereby routing the rectified vibration signal to peak hold B 132 for a second sample period of time beginning at time T+ΔT and ending at time T+2ΔT. This second sample period of time is immediately later than the first sample period of time so that the first and second sample periods of time, as well as all succeeding sample periods; of time (e.g., T+2ΔT to T+3ΔT, etc.), are contiguous with no dead time between sample periods. Analog switch 106 of peak hold B 132, having two closed positions, routes the rectified vibration signal while in a first closed position 106A to hold capacitor 120 and hold buffer 116, which hold the peak amplitude value for reading by the data collector 26 as described above with reference to peak hold A 130.

Analog switch 108, having two closed positions, alternately outputs on lines 109 the peak held amplitude values of buffers 114 and 116. When switch 108 is in a first closed position 108a, the output 109 is that value read from hold buffer 114 by the data collector 26. In similar fashion, when switch 108 is in a second closed position 108b, the output 109 is that value read from hold buffer 116 by the data collector 26. In a preferred embodiment, switches 102–108 are Siliconix DG419 analog switches. A sample rate, or clock signal on lines 111 enables appropriate switching timing for each of the switches 102–108, and thereby establishes a peak hold sample rate. In a preferred embodiment, the clock signal frequency on lines 111 is user selectable from 10 Hz, 20 Hz, 50 Hz, 100 Hz, 200 Hz, 500 Hz, 1,000 Hz, and 2,000 Hz.

When a switch is made to read one of the peak holds A or B, the other is reset by its corresponding reset device 110 or 112 within a few microseconds, typically about 25 microseconds, and then monitors for the next peak value. For example, when switch 108 is switched from its first closed position 108a to the second closed position 108b, reset device 110 operates through switch 104 to discharge hold capacitor 118. In a preferred embodiment, reset devices 110 and 112 are dual re-triggerable monostable, multivibrators with resets, such as the RCA CD54/74HCT123 multivibrator, with control timing provided by clock signal 111. The capacitor 118 and hold buffer 114 are reset in about 25 microseconds and then immediately begin monitoring again for the peak value during the next sample period of time. It will be appreciated that because of the brevity of the 25 microsecond reset time relative to the typical 5 millisecond impact duration time, there is no risk of missing an impact event during reset.

In like fashion, when switch 108 switches from the second closed position 108b to its first closed position 108a, reset device 112 operates through switch 106 to discharge hold capacitor 120, thereby resetting peak hold B for another sample period of peak monitoring. In this manner, the output 109 consists of the peak amplitude values of the rectified vibration signal and lags the impact by the selected sample time period duration.

The sample time period duration is user selectable through appropriate keypad 204 entries (FIG. 1) by selecting a desired clock signal frequency. The clock signal consists of pulses that are spaced to occur at the selected frequency. In a preferred embodiment, the clock signal has a 50% duty cycle where the leading edge of each pulse is used to initiate the sample period for peak hold A 130 and the trailing edge of each pulse is used to initiate the sample period of time for peak hold B 132 so that two sample periods of time occur for each clock pulse, or clock cycle. Therefore, the sample rate is double the clock frequency. For example, when a clock signal frequency of 10 Hz (100 msec) is selected, each sample period of time will last for 50 msec. Based on the clock signal frequency selection choices previously described, sample time period durations may be selected from 0.25 msec, 0.5 msec, 1.0 msec, 2.5 msec, 5.0 msec, 10 msec, 25 msec, and 50 msec.

The methodology of providing the data collector 26 with a pseudo-tachometer (PTach) signal representative of the speed of the target gear 36 for synchronous averaging with the peak held, output 109 will now be described in greater detail. Referring again to FIG. 1, a tachometer 30 is placed near the accessible output shaft 29 of gearbox 24, producing tachometer pulses on line 34 synchronously to the speed of the output shaft 29. The raw tachometer pulses represent angular position of the output shaft 29 and must accurately reflect the shaft's true angular position to be useful for the synchronous averaging. Therefore, the tachometer pulses are received by the pseudo-tachometer (PTach) circuit 200 of the signal processing unit 22 where they are appropriately adjusted and corrected, as will be described further, to accurately represent the true speed of the output shaft 29. The corrected output shaft pulses are then used to generate output pulses on line 218 where one output pulse is generated for each complete revolution of the target gear 36. Thus, from a computing point of view, reading the input pulses and generating the output pulses are two independent processes which exchange only the value of the current speed of the output shaft 29.

Although there are many different types of tachometers suitable for use with the present invention, a preferred embodiment employs an optical tachometer. Unfortunately, tachometers are often unreliable indicators of the true speed of the measured element. For example, a spec of oil or other debris on the reflective strip may cause two pulses to be generated, or may cause a pulse to be missed, or dropped entirely.

The input process of the PTach circuit 200 measures the time to complete each revolution of the output shaft 29 and observes incremental changes in speed during each succeeding revolution. A more accurate and clean tachometer signal is obtained by correcting the signal to eliminate added pulses and to compensate for dropped pulses. An error resulting from dropped or added pulses, or any other error, is assumed to have occurred if the time between two tachometer pulses indicates a change in speed of 25% or greater during one revolution. The PTach circuit 200 is programmed to ignore the "dropped" and "added" tachometer pulses that result in errors and to correct the signal by assuming that the measured element maintained some reasonable level of speed. If the current speed is within the expected range, an infinite impulse response, first order filter is used to clean up and stabilize the tachometer pulses by removing small oscillations and fluctuations, thus producing a new time (to complete one revolution of the output shaft 29) that will be used for the 25% speed comparison during the next succeeding revolution.

The filter formula is given by:

$$Yn = (K \times Xn) + ((1-K) \times Yn-1) \quad (1)$$

where: Yn represents the filtered time of the last revolution,

Yn−1 represents the filtered time of the next to last revolution,

Xn represents the elapsed time between the last two tachometer pulses, and

K represents a coefficient of filtration (depends on the ratio from setup).

Figure 6:
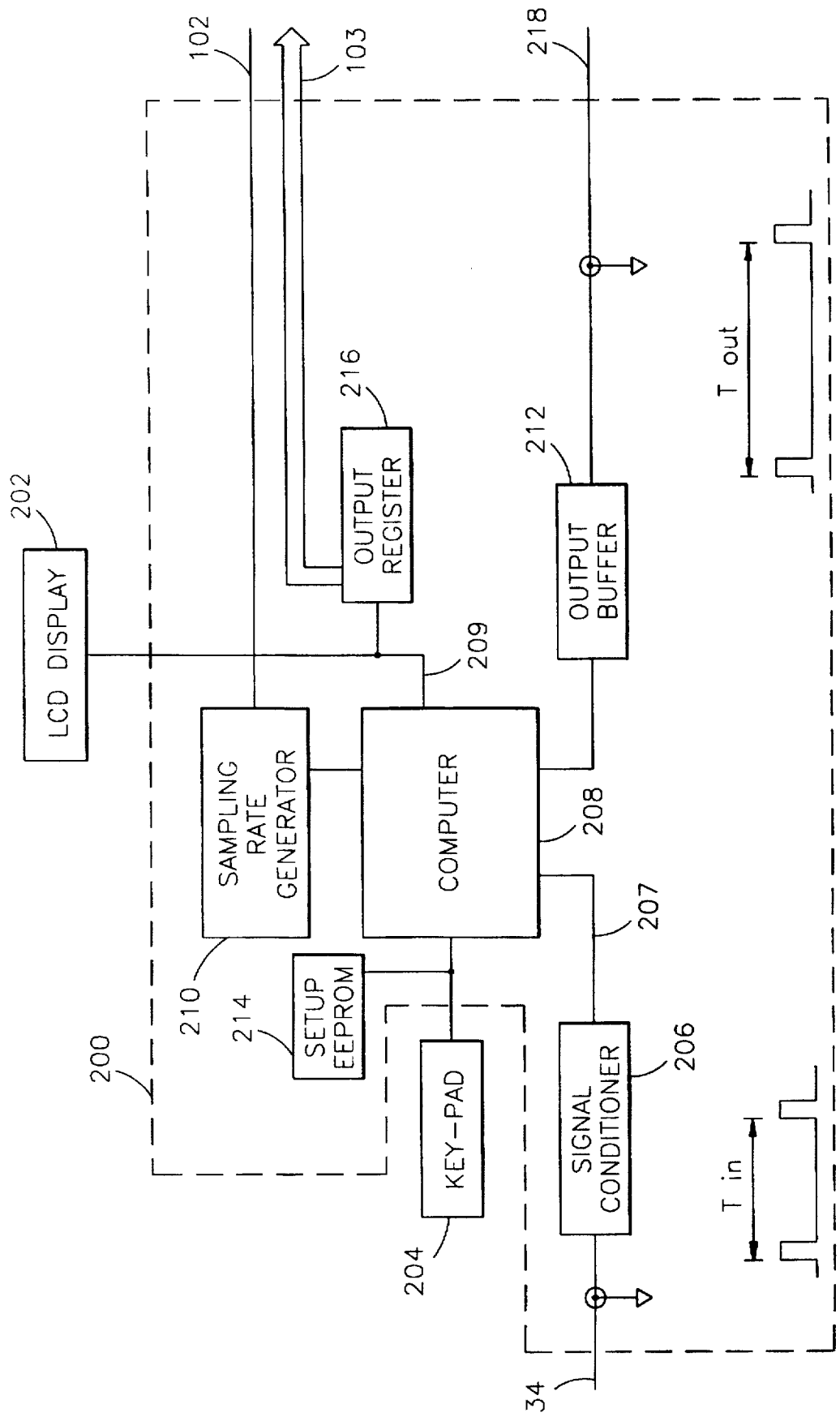
FIG. 6 is a block diagram of a pseudo-tachometer circuit.
Figure 7:
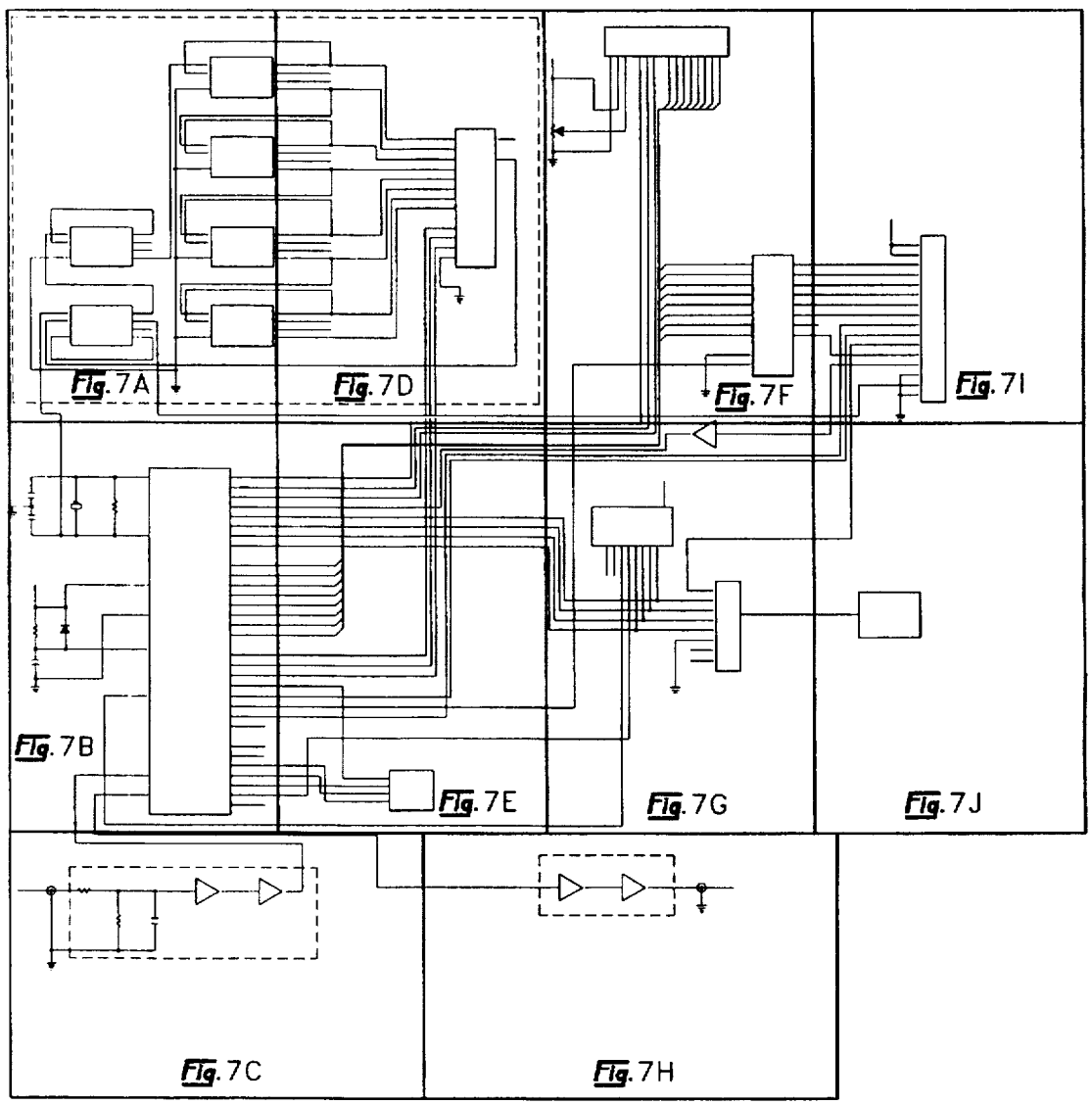
FIGS. 7 through 7J combine to provide a schematic circuit diagram of the pseudo-tachometer circuit; and on a gearbox having a cracked pinion tooth.
Figure 7B:
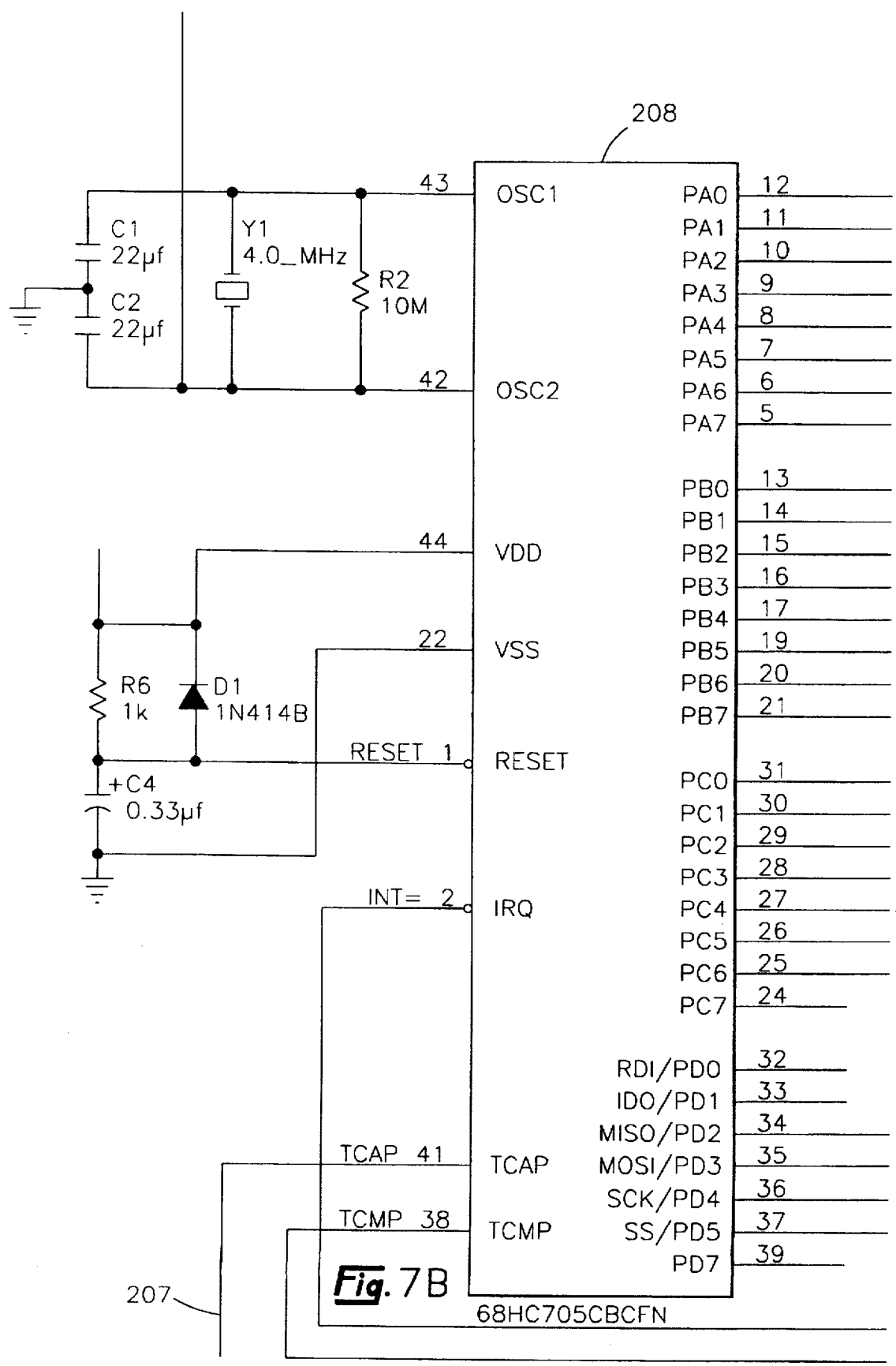
Figure 7C:
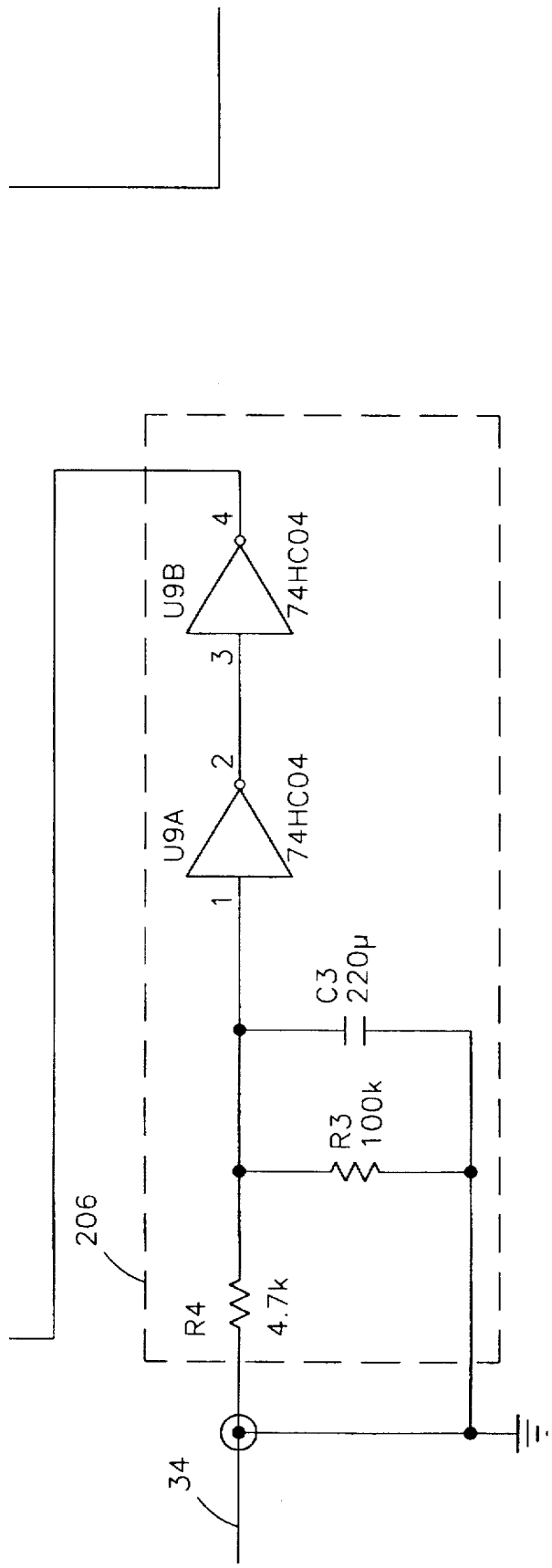
Figure 7D:
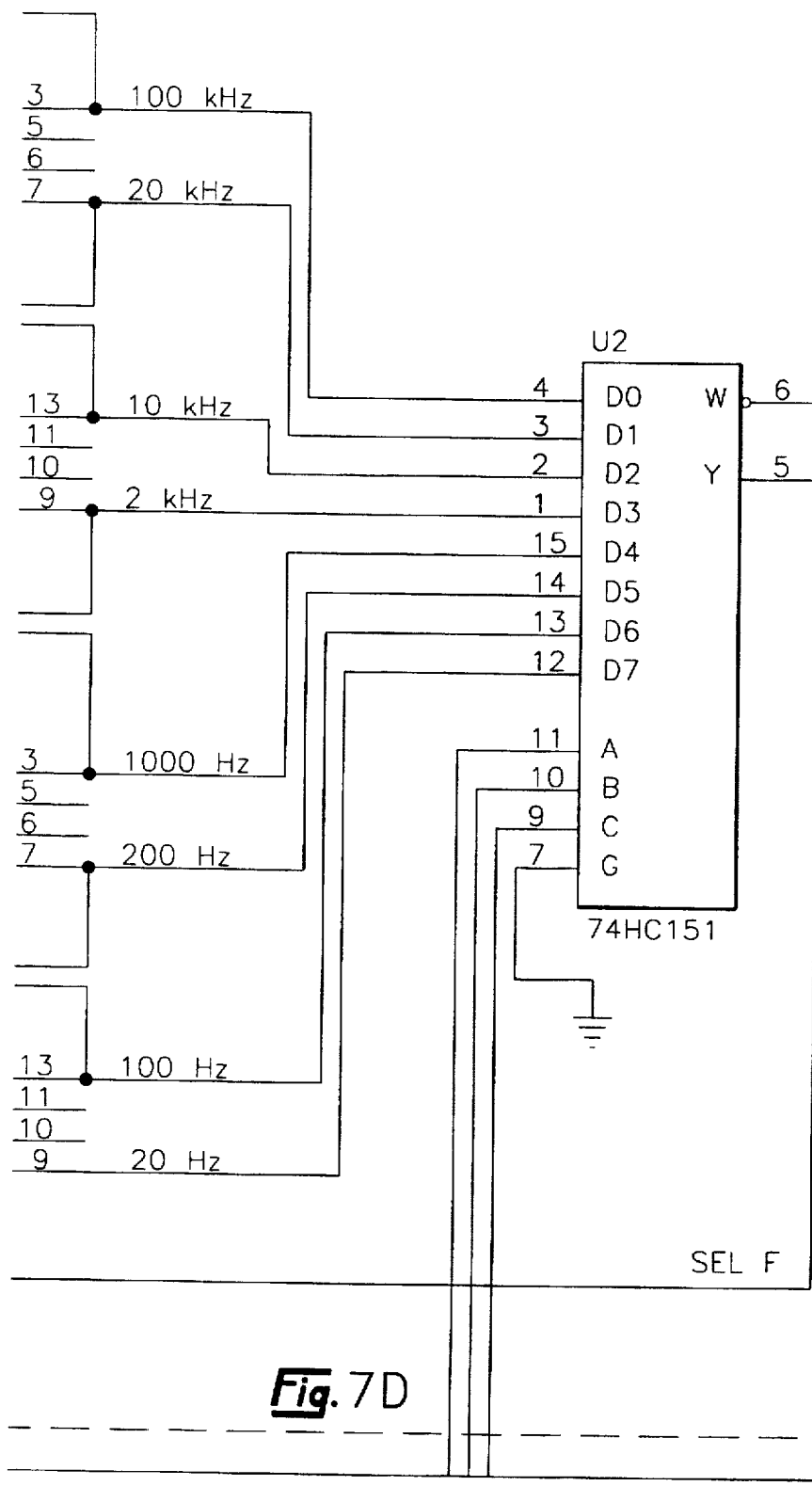
Figure 7E:
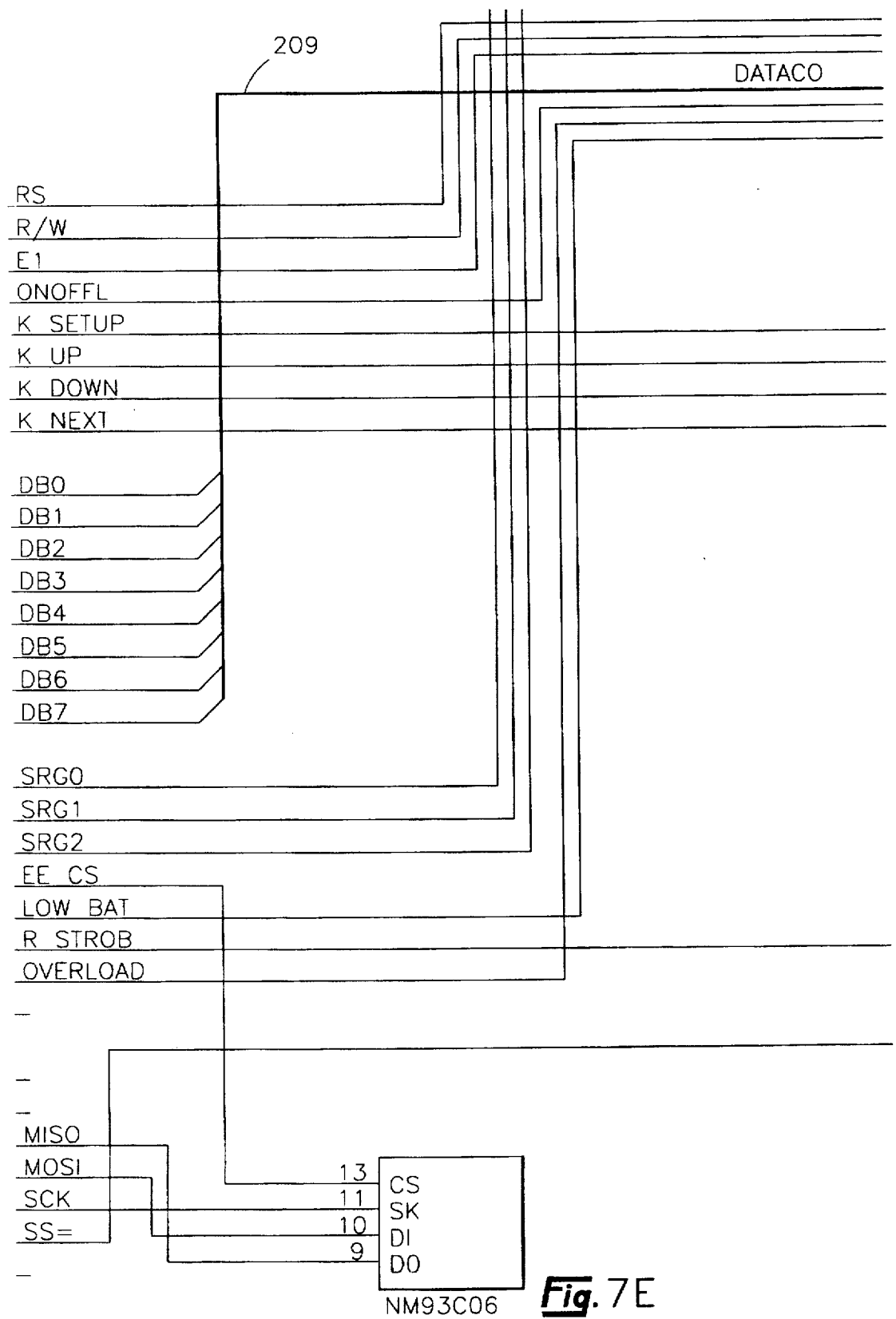
Figure 7F:
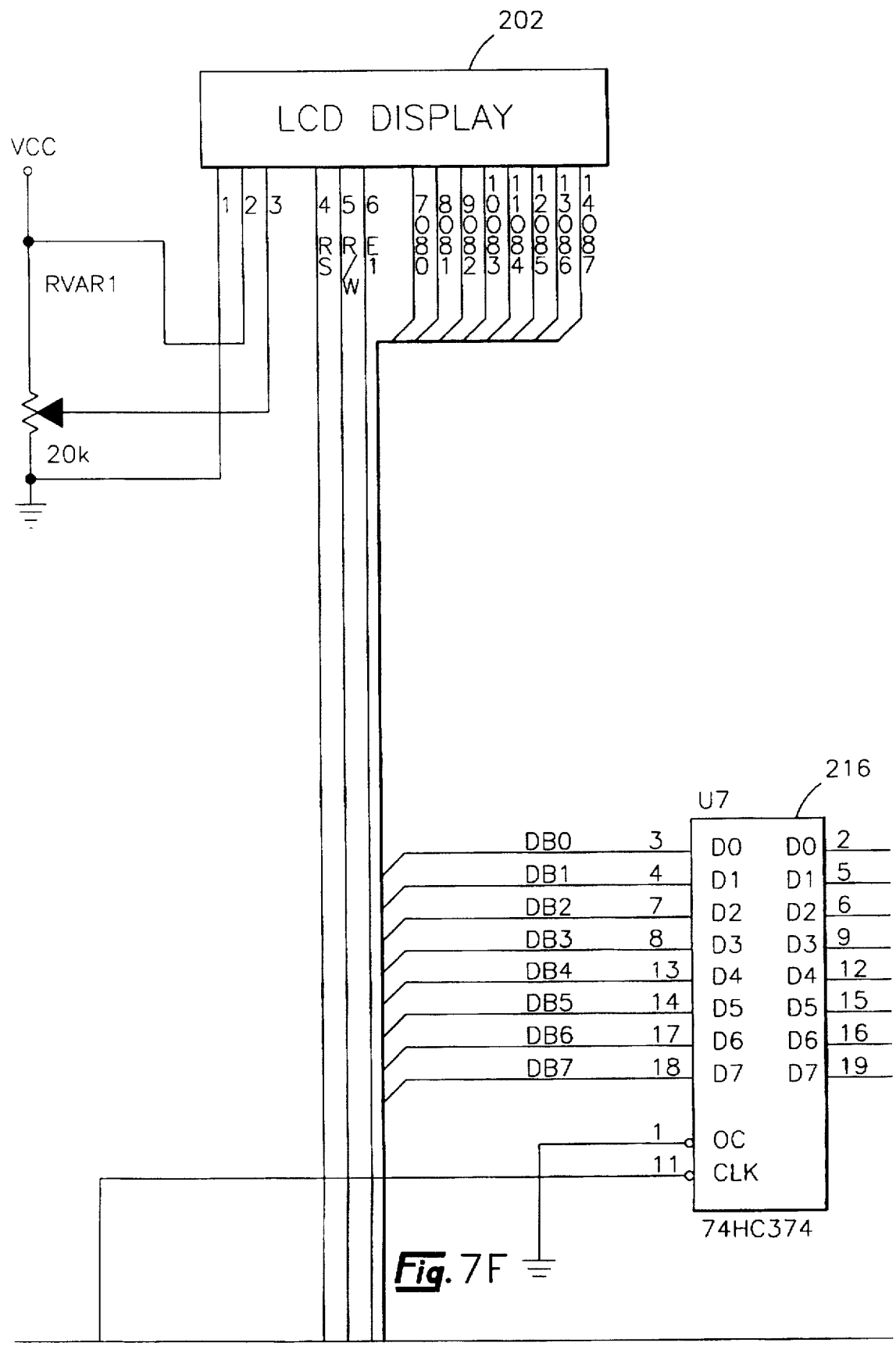
Figure 7G:
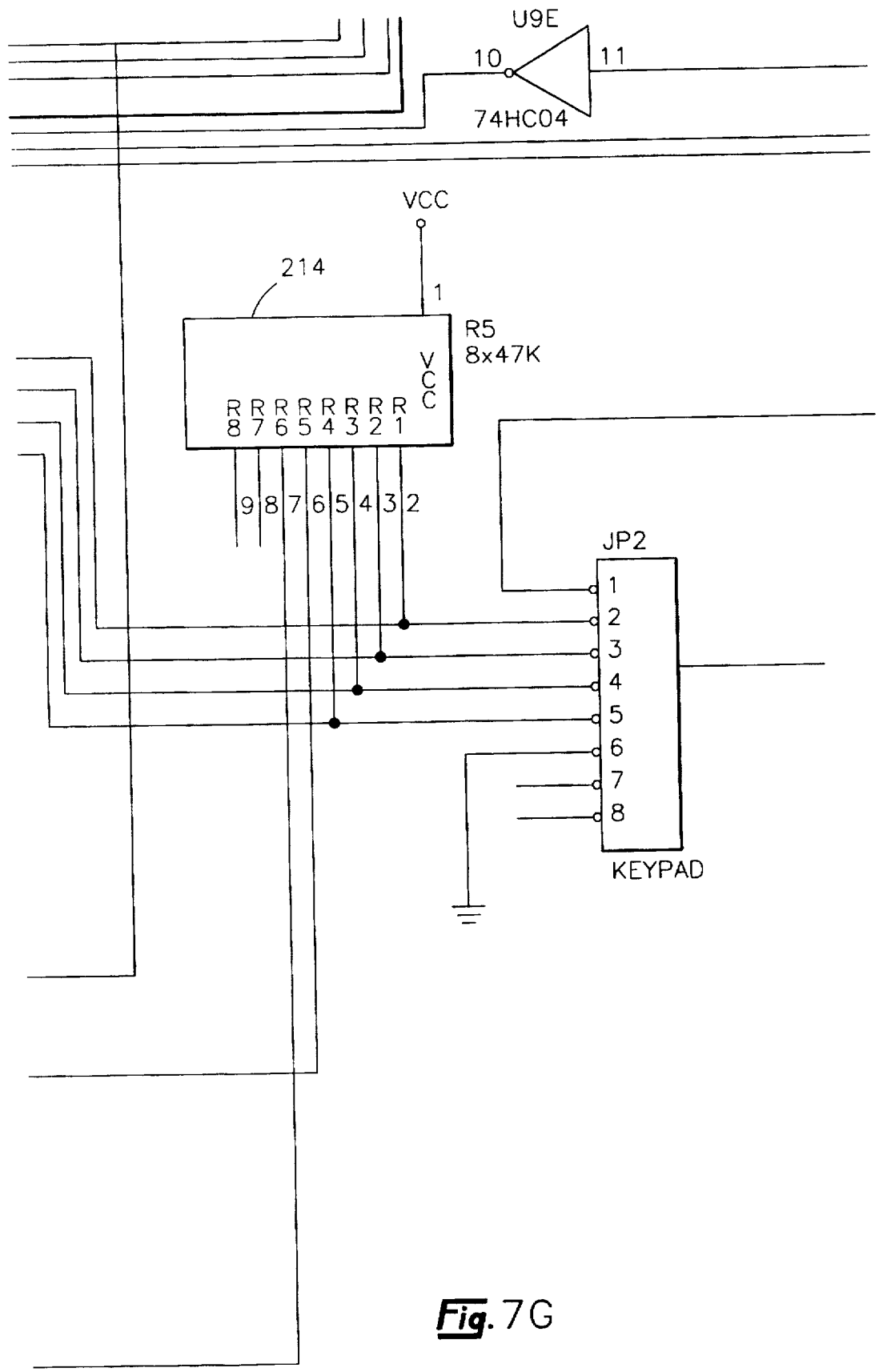
Figure 7H:
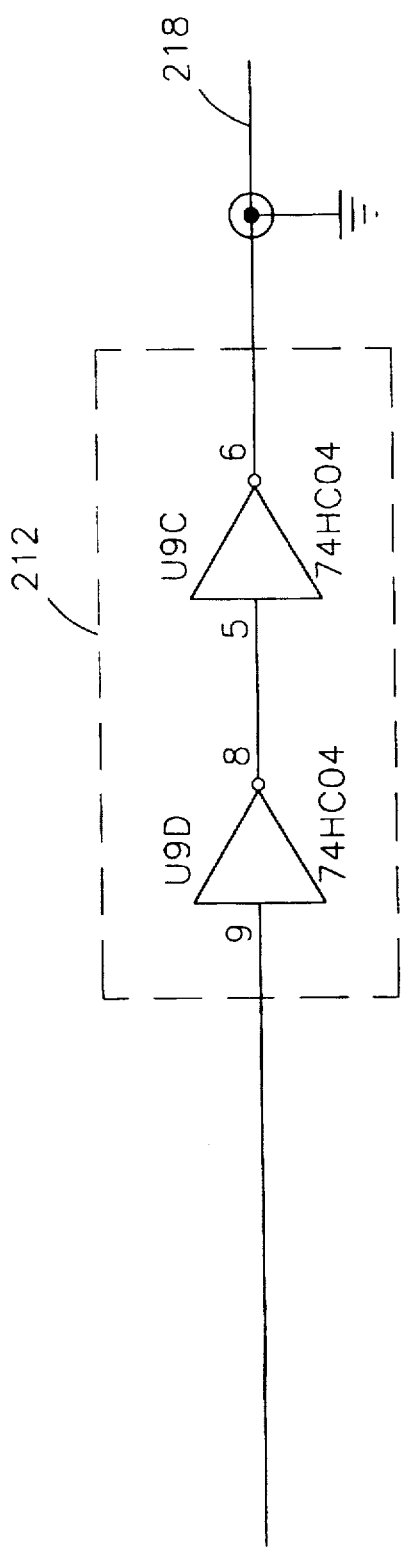
Figure 71:
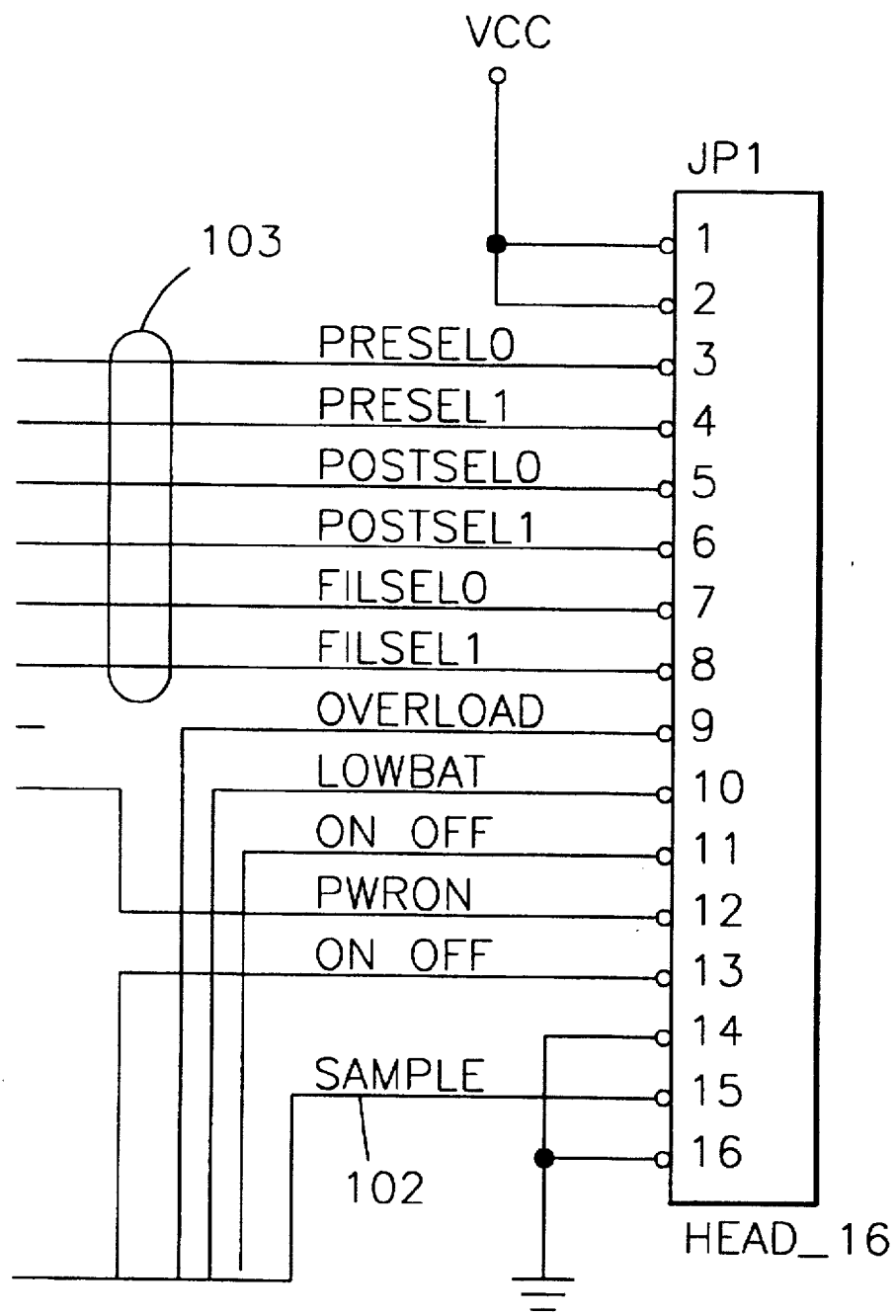

FIG. 6 provides a block diagram of the pseudo-tachometer circuit 200, and FIGS. 7 through 7J illustrate a more detailed schematic circuit diagram of the circuit 200. The output of tachometer 30 (FIG. 1) is received by a signal conditioner 206 where the raw tachometer signal is filtered for noise and buffered for input to a computer 208. In one embodiment, the computer is an 8-bit, 6800 series microprocessor. However, it will be understood that any microprocessor may be employed. The computer 208, which receives the conditioned tachometer signal on line 207, is programmed to perform a variety of functions, including the function of correcting and adjusting the tachometer signal to produce a PTach signal as previously described. The resulting PTach signal is sent to output buffer 212 where it is held and made available to the data collector 26 via line 218.

If an error is determined to have occurred, the computer programming initiates an error procedure. Upon detection of an error, the error procedure first increments an error counter by two (2). Each subsequent error increments the error counter by two. When the error counter reaches a value of eight (four errors), the counter will cause an interrupt in data acquisition and an error message will be displayed. An error occurs when a pulse width (elapsed time between pulses) indicates that the speed has changed by 25% or more. Therefore, an error can occur if the time between tachometer pulses is either "too long" or "too short".

If an error was cause by a "too long" pulse width time (dropped pulse), the error may be cleared from the error counter by the next succeeding pulses. The computer 208 is programmed to perform a 25% comparison on each tachometer pulse width and if the pulses following a "too long" error are within the expected range, the error counter is decremented by one (1). Two succeeding pulses that are within the 25% threshold will completely compensate for the one "dropped pulse" and return the error counter to zero. This procedure enables data acquisition to be maintained so long as the number of dropped pulses is less than one third of all incoming pulses.

If the PTach program receives a pulse which is too short, the pulse is ignored but 2 is added to the error counter and a low priority task termed "Double Pulse Eliminator" is activated. The Double Pulse Eliminator incorporates a special table which stores the four most recent pulses including the "too short" pulses marked with a special flag. This task, which runs only during computer idle times, computes the mean period from the four most recent pulses as though no "too short" pulses were ignored and no "too long" pulses were shortened. If the flagged pulse period is shorter than 75% of the mean value, the task confirms that the pulse period was, in fact, "too short" and subtracts two (2) from the error counter. In this way, even if, during each revolution, one pulse is added, the PTach circuit 200 can continue to provide an accurate PTach signal.

The PTach circuit 200 adjusts the corrected tachometer signal to produce a pseudo-tachometer signal representative of the speed of the inaccessible target gear 36 of the gearbox 24. This is accomplished when the gearbox 24 is operating at steady state by simply dividing the tachometer signal by the rotation ratio of the accessible element 29 to the target gear 36. comparative timers (not shown) are used to generate one pseudo-tachometer signal pulse for each revolution of the target gear 36. When the gearbox is not at steady state, e.g., is accelerating or decelerating, dynamic response characteristics of the timer can effect the accuracy of the pseudo-tachometer signal, particularly in applications involving a gearbox with speed reduction where one revolution on an input shaft produces less than one full revolution of the target gear 36.

For example, assume the rotation ratio of the input shaft 27 (which is being monitored with a tachometer) to the target gear 36 is 10:1. This means that ten revolutions of the input shaft 27 are required to produce one revolution of the target gear 36. If the input shaft 27 were to accelerate during its second revolution and continue accelerating through the tenth revolution, a large error will result in the pseudo-tachometer signal unless the timer is somehow corrected during the input shaft's acceleration. Therefore, to improve the dynamic response characteristics of the timer, the timer is corrected "on the fly" by observing the tachometer signal and adjusting the timer in proportion to any observed changes.

Computer 208 may also perform predictive speed monitoring when the rotation ration increases the output speed. In this case, the computer 208 must generate several pulses corresponding to the speed of the output shaft for each revolution of the input shaft. The pulses may be predicted, and a future speed curve may be generated, based on past speed.

The computer 208 also receives keypad 204 entries for setting appropriate test parameters, and provides user feedback and other information on the LCD display 202 via lines 209. Computer setup parameters, including rotation ratio, amplifier gains, filter bandpass, and sampling frequency, are stored in setup EEPROM 214 and can be changed by appropriate entries via the keypad 204. These parameter selections are received by the computer 208 and sent to an output register 216 via lines 209 where they are provided to the corresponding circuit elements on lines 103.

With continued reference to FIGS. 6, and 7 through 7J a sampling rate generator 210 provides the straightforward and essential function of generating a plurality of clock signal frequencies from which a desired sample time period and reset rate, as previously discussed, is selected by the user through appropriate keypad 204 entries. In a preferred embodiment, clock signal frequencies include 10 Hz, 20 Hz, 50 Hz, 100 Hz, 200 Hz, 500 Hz, 1,000 Hz, and 2,000 Hz. The clock signal frequency is output on line 111 and provided to the dual sample and peak value detector circuit 100 (FIG. 4) for switching and peak hold reset timing as previously discussed.

Referring again now to FIG. 4, the data collector 26 receives the peak held outputs 109 and PTach signal 218 and synchronously averages them to determine whether a fault is present in the monitored rotating element. The data collector 26, which has its own sample rate frequency, samples the peak held values of hold buffer 114 when switch 108 is in the first closed position 108a, and similarly samples the peak held values of hold buffer 116 when switch 108 is in the second closed position 108b. The peak held samples are synchronously averaged over time with the PTach signal so that the only peak held amplitudes which are not averaged out are those which regularly reappear at the same angular rate and at the same rotation speed as the PTach signal. These remaining synchronously averaged vibration signals can be transformed by a fast Fourier transform to the frequency domain to reveal the fundamental frequency of impact events.

The following Example is provided to help illustrate the described methodology and apparatus.

EXAMPLE

A reduction gearbox having a single internal shaft intermediate an input shaft and an output shaft was tested to determine the presence of mechanical faults on the internal shaft. The gearbox was driven by a 1 Hp DC motor with a relatively light load. The input shaft was a 16-tooth pinion driving an 88-tooth gear wheel on the intermediate shaft. The intermediate shaft had a 17-tooth pinion driving a 54-tooth gear wheel on the output shaft. Total speed reduction for this gearbox from input to output was calculated at: (16/88)(17/54)=17/297.

A cracked tooth was known to exist on one of the pinions.

To provide a vibration signal, an accelerometer was mounted in close proximity to the input shaft. To provide a tachometer signal, an optical tachometer was used to monitor the speed of the output shaft. The tachometer signal was multiplied by a rotation ratio of 17.471 to arrive at a pseudo-tachometer signal synchronized to the input shaft. It should be noted that, due to the presence of the computer 207 the signal processing unit 22 is programmed to receive either a ratio of integers (297/17) or floating point numbers to arrive at the pseudo-tachometer signal.

Figure 8A:
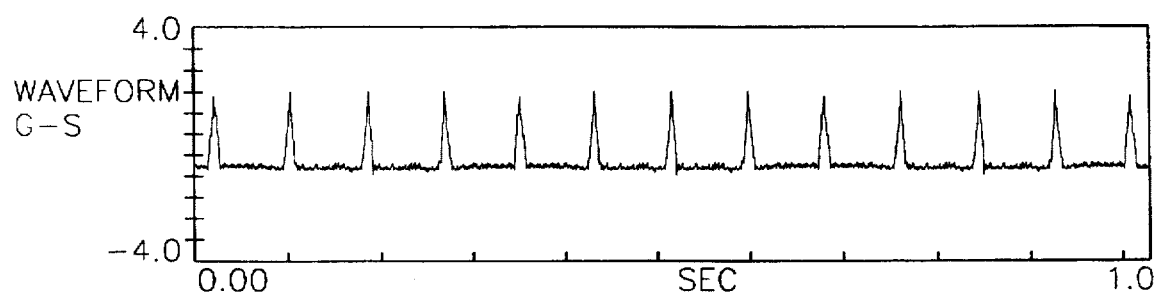
FIGS. 8A and 8B illustrate the results of a test performed on a gearbox having a cracked pinion tooth.
Figure 8B:
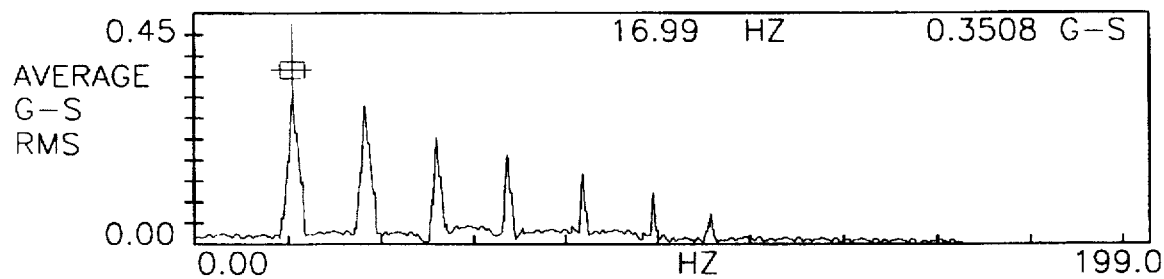

The results of synchronously averaging the peak held vibration values produced by FIG. 3 (line 109) with the pseudo-tachometer signal are shown in FIG. 8A. Transformation to the frequency domain, as shown in FIG. 8B, reveals a fundamental frequency of about 17 Hz with even harmonics of decreasing amplitude. The result of the synchronous averaging was to eliminate all random, asynchronous events and keep all events whose recurrence are synchronized to the rotational speed of the input shaft. Since the input shaft is rotating at a speed of about 17 Hz, the fundamental frequency peak indicates a synchronous impact is occurring once per revolution of the input shaft.

Rotation ratios for the intermediate and output shafts were also used to arrive at pseudo-tachometer signals each of these shafts (3.176 for the intermediate shaft and 1.00 for the output shaft). Synchronous averaging of the vibration signals with each of these pseudo-tachometer signals and transforming the results to the frequency domain as described above with reference to the input shaft revealed synchronous impact activity occurring 11 times per intermediate shaft revolution. However, these impacts were of less amplitude than those shown in FIG. 8B for the input shaft. There was no discernable impact activity associated with the output shaft.

Two possible fault scenarios exist based on these results. First, a tooth on the input shaft pinion is cracked or otherwise damaged. Second, a defective tooth on the input shaft pinion has damaged 11 teeth on the 88-tooth gear wheel and some impacting is occurring when each pinion tooth engages any of these 11. The combination of 16 teeth driving 88 teeth (prime number of 2 and 11) ensures that any specific tooth on the pinion will engage only 11 of the 88 teeth on the gear wheel.

It is contemplated, and will be apparent to those skilled in the art from the foregoing specification, drawings, and example that modifications and/or changes may be made in the embodiments of the invention. Accordingly, it is expressly intended that the foregoing are illustrative of preferred embodiments only, not limiting thereto, and that the true spirit and scope of the present invention be determined by reference to the appended claims.

What is claimed is:

1. A vibration analyzer for analyzing mechanical vibration produced by a machine to produce vibration analysis information corresponding to possible sources of the mechanical vibration, said analyzer comprising:

a vibration transducer for producing a transducer signal corresponding to the mechanical vibration;

an input circuit for receiving and conditioning the transducer signal to produce a vibration signal corresponding to said transducer signal;

a peak value detector for receiving the vibration signal, detecting the peak amplitude values of the vibration signal during each sample time period to produce a time series of peak vibration amplitudes, and outputting the time series of peak vibration amplitudes for further processing; and means for receiving the time series of peak vibration amplitudes and transforming said time series of peak vibration amplitudes to the frequency domain to produce peak vibration spectra.

2. The analyzer of claim 1, wherein said input circuit comprises:

an auto ranging amplifier for amplifying the transducer signal according to its strength, producing an amplified analog vibration signal;

a sampling circuit for receiving the amplified analog vibration signal and sampling it at a predetermined rate, producing a digitized vibration signal; and a rectifier for receiving the digitized vibration signal and digitally full wave rectifying it, producing a digitally rectified digital vibration signal that is provided to said peak value detector as the vibration signal.

3. The analyzer of claim 1 wherein said peak value detector comprises:

first peak hold means for holding the peak amplitude values of the vibration signal during a first sample time period T−ΔT;

second peak hold means for holding the peak amplitude values of the vibration signal during a second sample time period T+ΔT;

a first analog switch for receiving said vibration signal and alternately providing the vibration signal to the first peak hold means during time T−ΔT and to the second peak hold means during time T+ΔT;

a second analog switch for outputting the peak amplitude value held by the first peak hold means during time period T+ΔT, and outputting the peak amplitude value held by the second peak hold means during time period T−ΔT; and reset means for resetting the first peak hold means at time T−ΔT, and resetting the second peak hold means at time T.

4. The analyzer of claim 3, further comprising clock means for producing a clock signal, wherein said time periods T−ΔT and T+ΔT cumulatively comprise one cycle of said clock signal.

5. The analyzer of claim 3 wherein said first peak hold means comprise:

a first capacitor connected to receive said vibration signal during time period T−ΔT and hold the peak amplitude value as a first capacitor charge;

a first hold buffer connected to said first capacitor for holding the peak amplitude value as represented by said first capacitor charge; and a third analog switch having an open position and a closed position, connected to receive said vibration signal to pass the vibration signal to said first capacitor when said third analog switch is in the closed position.

6. The analyzer of claim 5 wherein said second peak hold means comprise:

a second capacitor connected to receive said vibration signal during time period T+ΔT and hold the peak amplitude value as a second capacitor charge;

a second hold buffer connected to said second capacitor for holding the peak amplitude value as represented by said second capacitor charge; and a fourth analog switch having an open position and a closed position, connected to receive said vibration signal and to pass the vibration signal to said second capacitor when said fourth analog switch is in the closed position.

7. A fault detection apparatus for receiving machine vibration and speed signals, processing said vibration signal to produce a processed vibration signal, and synchronously averaging the processed vibration signals at the speed indicated by the speed signal to determine the presence of a fault in a rotating element of the machine where the rotating element is rotating at the speed indicated by the speed signal, the apparatus comprising:

a peak value detector for receiving the machine vibration signal, sampling said vibration signal during predetermined sample time periods, and detecting the peak amplitude values of the vibration signal during the sample time periods, producing a time series of peak amplitude values;

clock means for generating at least one clock signal, said peak value detector being responsive to said at least one clock signal to set the length of said sample time periods; and means for synchronously averaging said time series of peak amplitude values at the speed of said rotating element, producing a time series of synchronously averaged amplitude values.

8. The apparatus of claim 7, further comprising:

an auto ranging amplifier for amplifying the vibration signal according to its strength, producing an amplified vibration signal;

a sampling circuit for receiving the amplified vibration signal and sampling it at a predetermined rate, producing a digitized vibration signal; and a rectifier for receiving the digitized vibration signal and full wave rectifying it, producing a rectified vibration signal that is provided to said peak value detector.

9. The apparatus of claim 7 wherein said peak value detector comprises:

first peak hold means for holding the peak amplitude value of the vibration signal during a first sample time period T−ΔT;

second peak hold means for holding the peak amplitude value of the vibration signal during a second sample time period T+ΔT;

a first analog switch for receiving said rectified vibration signal and alternately providing the vibration signal to the first peak hold means during time T−ΔT and to the second peak hold means during time T+ΔT;

a second analog switch for providing to the means for synchronously averaging the peak amplitude held by the first peak hold means during time period T+ΔT, and providing to the means for synchronously averaging the peak amplitude held by the second peak hold means during time period T−ΔT; and reset means for resetting the first peak hold means at time T−ΔT, and resetting the second peak hold means at time T.

10. The apparatus of claim 9 wherein said time periods T−ΔT and T+ΔT cumulatively comprise one cycle of said clock signal.

11. The apparatus of claim 7, further comprising a rectifier for rectifying the vibration signal.

12. The apparatus of claim 7, further comprising a filter for filtering selected frequencies from said vibration signal.

13. The apparatus of claim 7, further comprising an amplifier for amplifying said vibration signal.

14. The apparatus of claim 7, further comprising a pseudo-speed circuit for adjusting the speed signal to reduce errors and to compensate for a rotation ratio between an accessible rotating machine element and a target rotating machine element, producing a pseudo-speed signal corresponding to the speed of the target rotating machine element.

15. The apparatus of claim 14 wherein said pseudo-speed circuit comprises:

a filter for eliminating noise from the speed signal, producing a filtered speed signal;

a computer for receiving the filtered speed signal and adjusting the filtered speed signal to reduce errors and to compensate for said rotation ratio, producing a pseudo-speed signal; and an output buffer for holding the pseudo-speed signal so that it can be provided to said means for synchronously averaging.

16. The apparatus of claim 7, further comprising fast Fourier transform means for transforming said time series of synchronously averaged amplitude values to the frequency domain.

17. A fault detection system for detecting mechanical faults of machines having one or more rotating elements that generate mechanical vibrations while rotating, including an accessible element and a target element, the system comprising:

a vibration sensor for sensing vibrations generated by at least a target rotating machine element during machine operation, producing a vibration signal containing a plurality of amplitudes and frequencies;

a peak value detector for sampling said vibration signal during predetermined sample time periods and detecting the peak amplitude value of the vibration signal during the sample time periods, producing a time series of peak amplitude values;

clock means for generating at least one clock signal, said peak value detector being responsive to said at least one clock signal to set the length of said sample time periods;

a speed sensor for sensing the speed of an accessible rotating machine element, producing a speed signal;

a pseudo-speed circuit for adjusting the speed signal to reduce errors and to compensate for a rotation ratio between the accessible rotating machine element and the target rotating machine element, producing a pseudo-speed signal; and means for reading said time series of peak amplitude values, receiving said pseudo-speed signal, and synchronously averaging said time series of peak amplitude values at the speed indicated by said pseudo-speed signal, producing a time series of synchronously averaged amplitude values corresponding to possible sources of the mechanical vibration.

18. The system of claim 17, further comprising:

an auto ranging amplifier for amplifying the vibration signal according to its strength, producing an amplified vibration signal;

a sampling circuit for receiving the amplified vibration signal and sampling it at a predetermined rate, producing a digitized vibration signal; and a rectifier for receiving the digitized vibration signal and full wave rectifying it, producing a rectified vibration signal that is provided to said peak value detector.

19. The system of claim 17 wherein said peak value detector comprises:

first peak hold means for holding the peak amplitude value of the vibration signal during a first sample time period $T-\Delta T$;

second peak hold means for holding the peak amplitude value of the vibration signal during a second sample time period $T+\Delta T$;

a first analog switch for receiving said vibration signal and alternately providing the vibration signal to the first peak hold means during time $T-\Delta T$ and to the second peak hold means during time $T+\Delta T$;

a second analog switch for providing to the means for reading the peak amplitude value held by the first peak hold means during time period $T+\Delta T$, and providing to the means for reading the peak amplitude value held by the second peak hold means during time period $T-\Delta T$; and reset means for resetting the first peak hold means at time $T-\Delta T$, and resetting the second peak hold means at time $T$.

20. The system of claim 19 wherein said time periods $T-\Delta T$ and $T+\Delta T$ cumulatively comprise one cycle of said clock signal.

21. The system of claim 17, further comprising a rectifier for rectifying the vibration signal.

22. The system of claim 17, further comprising a filter for filtering selected frequencies from said vibration signal.

23. The system of claim 17, further comprising an amplifier for amplifying said vibration signal.

24. The fault detection system of claim 17 wherein said speed sensor comprises a tachometer.

25. The fault detection system of claim 17 wherein said pseudo-speed circuit comprises:

a filter for eliminating noise from the speed signal, producing a filtered speed signal;

a microcomputer for receiving the filtered speed signal and adjusting the filtered speed signal to reduce errors and to compensate for said rotation ratio, producing a pseudo-speed signal; and an output buffer for holding the pseudo-speed signal so that it can be read by a peripheral device.

26. A method of processing, for further analysis, a vibration signal generated by a vibration sensor attached to a machine, the method comprising the steps of:

determining the peak amplitude value of the vibration signal with a peak value detector during sample time periods, producing a time series of peak vibration amplitudes;

transforming said time series of peak vibration amplitudes to the frequency domain to produce peak vibration spectra; and outputting the peak vibration spectra for further processing.

27. The method of claim 26, further comprising the steps of:

auto range amplifying the vibration signal according to the strength of the vibration signal, producing an amplified vibration signal;

sampling the amplified vibration signal at a predetermined rate to produce a digitized vibration signal; and rectifying the digitized vibration signal, producing a rectified digital vibration signal that is provided to the peak value detector.

28. A method of detecting faults in a machine having rotating machine elements, said elements including at least an accessible element and a target element, said method comprising the steps of:

producing a vibration signal containing amplitudes and frequencies, said vibration signal being representative of vibrations generated by at least the target rotating machine element;

sampling said vibration signal during predetermined sample periods of time;

determining the peak amplitude value of said vibration signal during each sample period of time to produce a time series of peak amplitude values;

producing a speed signal with a speed sensor, said speed signal being representative of the speed of the target element as sensed by said speed sensor;

synchronously averaging said time series of peak amplitude values at the speed indicated by said speed signal, producing a time series of synchronously averaged amplitude values; and transforming the time series of synchronously averaged amplitude values to the frequency domain to determine the presence of a fault in the target element.

29. The method of claim 28, further comprising the step of adjusting the speed signal to reduce errors and to compensate for a rotation ratio between the first rotating machine element and the target rotating machine element, producing a pseudo-speed signal representing the speed of the target element.

30. The method of claim 26, further comprising the step of analyzing said peak vibration spectra for possible machine faults.

* * * * *